US 008551756B2

United States Patent
Smith et al.

(10) Patent No.: US 8,551,756 B2
(45) Date of Patent: *Oct. 8, 2013

(54) AVIAN INFLUENZA CHIMERIC VLPS

(75) Inventors: Gale Smith, Rockville, MD (US); Peter Pushko, Frederick, MD (US)

(73) Assignee: Novavax, Inc., Rockville, MD (US)

( * ) Notice: Subject to any disclaimer, the term of this patent is extended or adjusted under 35 U.S.C. 154(b) by 550 days.

This patent is subject to a terminal disclaimer.

(21) Appl. No.: 12/689,826

(22) Filed: Jan. 19, 2010

(65) Prior Publication Data

US 2010/0184192 A1 Jul. 22, 2010

Related U.S. Application Data

(63) Continuation of application No. PCT/US2008/070638, filed on Jul. 21, 2008, and a continuation-in-part of application No. 10/617,569, filed on Jul. 11, 2003.

(60) Provisional application No. 60/950,707, filed on Jul. 19, 2007, provisional application No. 60/970,592, filed on Sep. 7, 2007, provisional application No. 61/071,835, filed on May 20, 2008.

(51) Int. Cl.
*C12N 7/00* (2006.01)
*C12N 7/04* (2006.01)

(52) U.S. Cl.
USPC ........ 435/235.1; 435/69.1; 435/236; 435/239

(58) Field of Classification Search
None
See application file for complete search history.

(56) References Cited

U.S. PATENT DOCUMENTS 7,556,940 B2 * 7/2009 Galarza et al. ............... 435/69.3
8,080,255 B2 * 12/2011 Smith et al. ............... 424/210.1

FOREIGN PATENT DOCUMENTS

WO WO 2005/020889 A2 3/2005
WO WO2007047831 4/2007

OTHER PUBLICATIONS

Pushko, et al., Influenza virus-like particles comprised of the HA, NA, and M1 proteins of H9N2 influenza virus induce protective immune responses in BALB/c mice, Vaccine, vol. 23, Issue 50, Dec. 30, 2005, pp. 5751-5759.*
Bright et al., "Influenza virus-like particles elicit broader immune responses than whole virion inactivated influenza virus or recombinant hemagglutinin,", Vaccine 25(19):3871-3878(2007).
Georg, "Supplementary European Search Report," 9 pages, EP appl. No. 08782139 (Sep. 2, 2011).
Gomez-Puertas et al., "Influenza Virus Matrix Protein is the Major Driving Force in Virus Budding," J. Virol. 74(24):11538-11547 (2000).
Latham and Galarza, "Formation of Wild-Type and Chimeric Influenza Virus-Like Particles following Simultaneous Expression of Only Four Structural Proteins," J. Virol. 75(13):6154-6165 (2001).
Pushko et al., "Influenza virus-like particles comprised of the HA, NA, and M1 proteins of H9N2 influenza virus induce protective immune responses in BALB/c mice," Vaccine 23(50):5751-5759 (2005).
PCT/US2008/70638. Applicant: Novavax, Inc. Int'l Search Report—Written Opinion (Nov. 18, 2008).
McQueen et al. "Polarized expression of a chimeric protein in which the transmembrane and cytoplasmic domains of the influenza virus hemagglutinin have been replaced by those of the vesicular stomatitis virus G protein." Proc. Nat. Acad. Sci. USA:83, 9318-9322 (Dec. 1986).
Giroglou et al. "Retroviral vectors pseudotyped with severe acute respiratory syndrome coronavirus S protein." J. Virol. 78:17, 9007-9015 (Sep. 2004).
Wood et al. "Reference viruses for seasonal and pandemic influenza vaccine preparation." www.blackwellpublishing.com/influenza (Dec. 2006).
Bukreyev et al., Mucosal immunisation of African green monkeys (*Cercopithecus aethiops*) with an attenuated parainfluenza virus expressing the SARS coronavirus spike protein for the prevention of SARS. Lancet Jun. 26, 2004, 363.

* cited by examiner

*Primary Examiner* — Mary E Mosher
*Assistant Examiner* — Myron Hill
(74) *Attorney, Agent, or Firm* — Cooley LLP

(57) ABSTRACT

This invention discloses a method of increasing production of virus-like particles comprising expressing an avian influenza matrix protein. The invention also comprises methods of making and using said VLPs.

15 Claims, 15 Drawing Sheets

Figure 5

```
   1 MFIFLLFIFL TSGSPDLORCT TPDDVQAPNY TQHTSSMRGV YYPDEIFRSD TLYLTQDLFL
  61 PFYSNVTGFH TINHFFGNPV IPFKDGIYFA ATEKSNVVRG WVFGSTMNNK SQSVIINNS
 121 TNVVIRACNF ELCDNPFFAV SKPMGTQHT MIFDMAFNCT FEYISDAFSL DVSEKSGRFK
 181 HLREFVFKNK DGFLYVKGY QPIDVVRDLP SGFNTLKPIF KLPLGINITN FRAILHAFSP
 241 AQDIWGTSAA AYFVGYLKPT TPMLKYDENG TITDAVDCSQ NPLAELKCSV KSFEIDKGIY
 301 QTSNFRVVPS GDVVRFPNIT NLCPFGEVEN ATKFPSVYAW ERKKISNCVA DYSVLYNSTF
 361 FSTFKCYGVS ATKLNDLCFS NVYADSFVVK GDDVRQIAPG QTGVIADYNY KLPDDFMGCV
 421 LAWNTRNIDA TSTGNYNYKY RYLRHGKLRP FERDISNVPF SPDGKPCTPP ALNCYWPLND
 481 YGFYTTTGIG YQPYRVTVLS FELLNAPATV CGPKLSTDLI KNQCVNFNFN GLTGTGVLTP
 541 SSKRFQPFQQ FGRDVSDFTD SVRDPKTSEI LDISPCSFGG VSVITPGTNA SSEVAVLYQD
 601 VNCTDVSTAI HADQLTPAWR IYSTGNNVFQ TQAGCLIGAE HVDTSYECDI PIGAGICASY
 661 HTVSLLRSTS QKSIVAYTMS LGADSSIAYS NNTIAIPTNF SISITTEVMP VSMAKTSVDC
 721 NMYICGDSTE CANLLLQYGS FCTQLNRALS GIAAEQDRNT REVFAQVKQM YKTPTLKYFG
 781 GFNFSQILPD PLKPTKRSFI EDLLFNKVTL ADAGFMKQYG ECLGDINARD LICAQRFNGL
 841 TVLPFLLTDD MIAAYTAALV SGTATAGWTF GAGAALQIPF AMQMAYRFNG IGVTQNVLYE
 901 MQKQIANQFN KAISQIQESL TTTSTALGKL QDVVNQNAQA LNTLVKQLSS NFGAISSVLN
 961 DILSRLDKVE AEVQIDRLIT GRLQSLQTYV TQQLIRAAEI RASANLAATK MSECVLGQSK
1021 RVDFCGKGYH LMSFPQAAPH GVVFLHVTYV PSQERNFTTA PAICHEGKAY FFREGVFVFN
1081 GTSWFITQRN FFSPQITTD NTFVSGNCDV VIGIINNTVY DPLQPELDSF KEELDKYFKN
1141 HTSPDVDLGD ISGINASVVN IQKEIDRLNE VAKNLNESLI DLQELGKYEQ YIKWPQILSI
1201 YSTVASSLAL AIMMAGLSLW MCSNGSLQCR ICI (SEQ ID NO. 10)
```

Figure 6

```
  1 MSLLTEVETYVLSIIPSGPLKAEIAQKLEDVFAGKNTDLEALMEWLKTRP
 51 ILSPLTKGILGFVFTLTVPSERGLQRRRFVQNALNGNGDPNNMDRAVKLY
101 KKLKREITFHGAKEVSLSYSTGALASCMGLIYNRMGTVTTEVAFGLVCAT
151 CEQIADSQHRSHRQMATITNPLIRHENRMVLASTTAKAMEQMAGSSEQAA
201 EAMEVANQARQMVQAMRTIGTHPNSSAGLRDNLIENLQAYQKRMGVQMQR
251 FK (SEQ ID NO. 3)
```

Influenza B/Florida/4/06 VLP Constructs

Wild Type: PolH—M1, PolH—HA, PolH—NA

Reassortant: PolH—M1, PolH—HA, PolH—NA (third row): M1, HA, NA

Reagent: HA, NA

Figure 15

Influenza B/Florida/4/06

Avian M1 (BV538)

B/AA M1 (BV539)

wt M1 (BV540)

AVIAN INFLUENZA CHIMERIC VLPS

CROSS REFERENCE TO RELATED APPLICATIONS

The present application is a continuation under 35 U.S.C. §120 and 35 U.S.C. §365(c) of International Application PCT/US2008/070638, filed Jul. 21, 2008, which claims the benefit of U.S. Provisional Application No. 60/950,707, filed Jul. 19, 2007, U.S. Provisional Application No. 60/970,592; filed Sep. 7, 2007, and U.S. Provisional Application No. 61/071,835, filed May 20, 2008, all of which are herein incorporated by reference in their entireties for all purposes. This application also claims priority under 35 U.S.C. §120 as a continuation-in-part of U.S. Ser. No. 10/617,569, filed Jul. 11, 2003, which is incorporated herein by reference in its entirety for all purposes.

A portion of this invention was made with government support under contract RFA-AI-03-016 awarded by the Department of Health and Human Services. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing of the Sequence Listing (filename: NOVV 016 02US SeqList_ST25.txt, date recorded: Apr. 5, 2010, file size 54 kilobytes).

BACKGROUND OF THE INVENTION

Influenza virus is a member of Orthomyxoviridae family (for review, see Murphy and Webster, 1996). There are three subtypes of influenza viruses designated A, B, and C. The influenza virion contains a segmented negative-sense RNA genome. The influenza virion includes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2) proteins. The HA, NA, M1, and M2 are membrane associated, whereas NP, PB1, PB2, PA, and NS2 are nucleocapsid associated proteins. The NS1 is the only nonstructural protein not associated with virion particles but specific for influenza-infected cells. The M1 protein is the Most abundant protein in influenza particles. The HA and NA proteins are envelope glycoproteins, responsible for virus attachment and penetration of the viral particles into the cell, and the sources of the major immunodominant epitopes for virus neutralization and protective immunity. Both HA and NA proteins are considered the most important components for prophylactic influenza vaccines because they are highly immunogenic.

To date, all commercially available influenza vaccines for non-pandemic strains in the United States have been propagated in embryonated hen's eggs. Although influenza virus grows well in hen's eggs, production of vaccine is dependent on the availability of eggs. Supplies of eggs must be organized, and strains for vaccine production selected months in advance of the next flu season, limiting the flexibility of this approach, and often resulting in delays and shortages in production and distribution. Unfortunately, some influenza vaccine strains, do not replicate well in embryonated chicken eggs, and have to be isolated by cell culture in a costly and time consuming procedure.

Systems for producing influenza viruses in cell culture have also been developed in recent years (See, e.g., Furminger. Vaccine Production, in Nicholson et al. (eds) Textbook of Influenza pp. 324-332; Merten et al. (1996) Production of influenza virus in cell cultures for vaccine preparation, in Cohen & Shafferman (eds) Novel Strategies in Design and Production of Vaccines pp. 141-151). Typically, these methods involve the infection of suitable immortalized host cells with a selected strain of virus. While eliminating many of the difficulties related to vaccine production in hen's eggs, not all pathogenic strains of influenza grow well and can be produced according to established tissue culture methods. In addition, many strains with desirable characteristics, e.g., attenuation, temperature sensitivity and cold adaptation, suitable for production of live attenuated vaccines, have not been successfully grown in tissue culture using established methods. In addition, live attenuated viruses have not been accepted by the general public due to fears reversion to a virulent virus.

Virus like particles mimic the overall structure of a virus particle without the requirement of containing infectious material. VLPs lack a viral DNA or RNA genome, but retain the three-dimensional structure of an authentic virus. VLPs have the ability to stimulate B-cell mediated responses, CD4 proliferative responses and cytotoxic T lymphocytes responses (see, Schirmbeck el al. (1996) Eur. J. Immunol., 26, 2812-2822). In addition, virus like particles induce MHC class I-restricted T-cell responses.

SUMMARY OF THE INVENTION

The present invention comprises a method of increasing the efficiency of influenza VLP production comprising expressing an avian influenza M1 and at least one non-avian influenza protein in a host cell. In one embodiment, said VLP comprises HA and/or NA from a non-avian influenza virus. In another embodiment, said non-avian influenza protein is a seasonal influenza protein. In another embodiment, said HA or NA have hemaggutinin and neuraminidase activity, respectfully. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of avian or heterologous influenza HA and/or NA.

The present invention also comprises a chimeric VLP comprising an avian influenza M1 protein and at least one non-avian influenza protein. In one embodiment, said non-avian influenza protein is HA and/or NA from a non-avian influenza virus. In another embodiment, said non-avian influenza protein is a seasonal influenza protein. In another embodiment, said HA or NA has hemaggutinin or neuraminidase activity, respectfully. In another embodiment, said HA and/or NA are chimeric proteins. In another embodiment, chimeric proteins comprise external domains of non-avian influenza HA and/or NA protein sequences fused to the transmembrane and/or cytoplasmic-terminal domains of the avian or heterologous influenza HA and/or NA. In another embodiment, said non-avian influenza protein is from an infectious agent.

The present invention also comprises an antigenic formulation comprising a chimeric VLP comprising an avian influenza M1 protein and at least one non-avian influenza protein. In one embodiment, said VLP comprises HA and/or NA from a non-avian influenza virus. In another embodiment, said HA or NA have hemagglutinin and neuraminidase activity, respectfully. In another embodiment, said HA and/or NA are chimeric proteins.

The present invention also comprises vaccines comprising a chimeric VLP comprising an avian influenza M1 protein and at least one non-avian influenza protein. In one embodiment, said VLP comprises HA and/or NA from a non-avian influenza virus. In another embodiment, said HA or NA have hemagglutinin and neuraminidase activity, respectfully. In another embodiment, said HA and/or NA are chimeric proteins.

The present invention also comprises a method of inducing immunity in a vertebrate comprising administering to said vertebrate a chimeric VLP comprising an avian influenza M1 protein and at least one non-avian influenza protein. In one embodiment, said immune response is a humoral immune response. In one embodiment, said immune response is a cellular immune response.

The present invention also comprises a method of preventing and/or reducing a viral infection or symptom thereof, comprising administering to a vertebrate a chimeric VLP comprising an avian influenza M1 protein and at least one non-avian influenza protein.

The present invention also comprises a method of reducing the severity of influenza in a population, comprising administering the a chimeric VLP comprising an avian influenza M1 protein and at least one non-avian influenza protein to enough individuals in said population in order to prevent or decrease the chance influenza virus transmission to another individual in said population.

BRIEF DESCRIPTION OF THE FIGURES

FIG. 5 depicts the amino acids sequence of SARS S protein with Indonesia H5N1 HA transmembrane and carboxyl terminal domain (underlined).

FIG. 6 depicts the amino acids sequence of Indonesia H5N1 M1 protein.

FIG. 7 depicts pFastBac 1 vector containing coding sequences for SARS S with Indonesia H5N1 HA TM/CT domain and Indonesia H5N1 M1 protein.

FIG. 13 depicts expression constructs for production of B/Florida/4/06 VLPs in Sf9 insect cells. Shown are the location of HA, NA, and M1 genes, as well as locations of polyhedron promoter. Also shown are the constructs for individual expression of HA and NA genes for reagent purposes.

FIG. 15 depicts Electron microscopy of purified VLPs. Negative staining transmission electron microscopy of influenza B/Florida/4/06 VLPs containing M1 from A/Indonesia/5/05 (H5N1) (left), B/Ann Arbor/1/1986 (middle), and B/Florida/4/06 (right).

DETAILED DESCRIPTION

Figure 1:
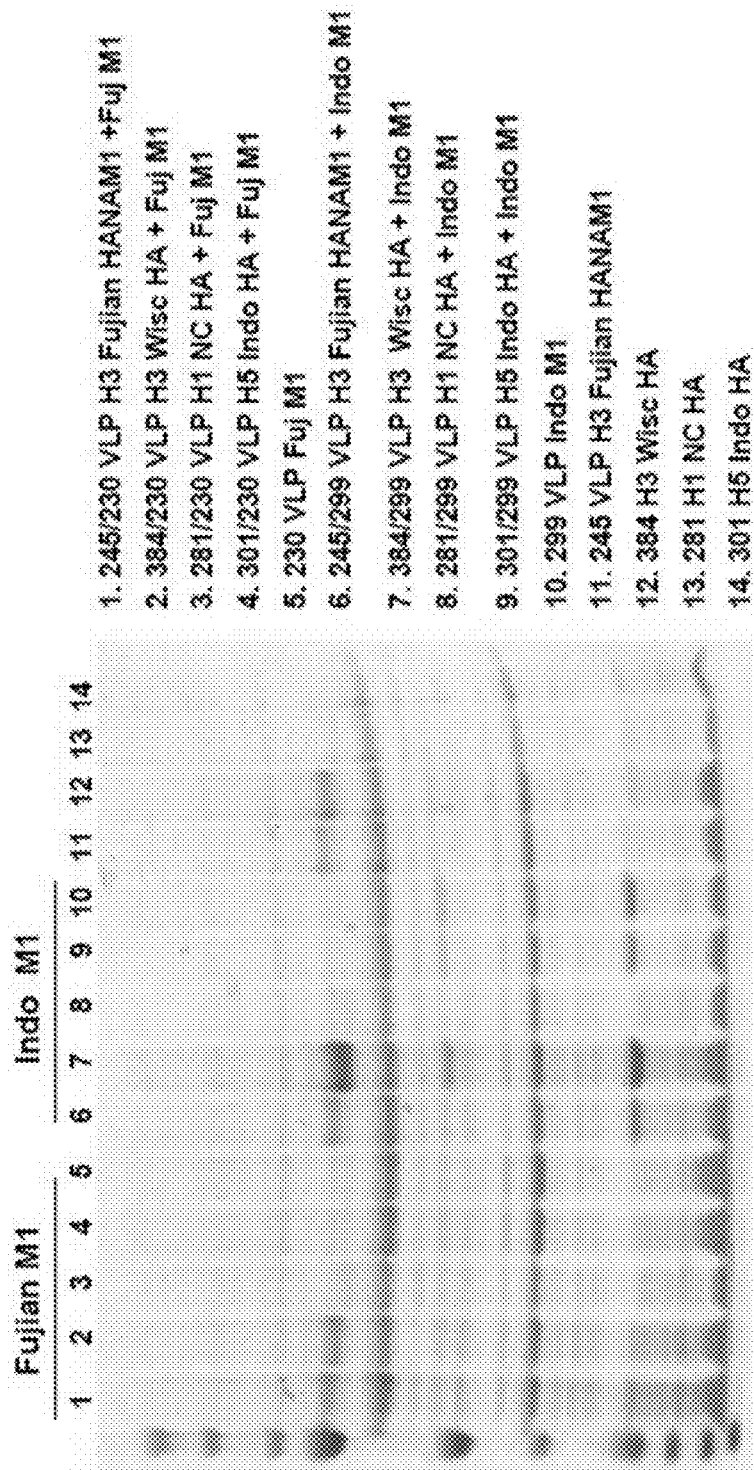
FIG. 1 depicts a stained SDS-PAGE gel derived from VLPs made from different constructs after isolation from a sucrose gradient.

As use herein, the term "antigenic formulation" or "antigenic composition" refers to a preparation which, when administered to a vertebrate, especially a bird or a mammal, will induce an immune response.

As used herein the term "adjuvant" refers to a compound that, when used in combination with a specific immunogen (e.g. a VLP) in a formulation, augments or otherwise alters or modifies the resultant immune response. Modification of the immune response includes intensification or broadening the specificity of either or both antibody and cellular immune responses. Modification of the immune response can also mean decreasing or suppressing certain antigen-specific immune responses.

As used herein the term "avian influenza virus" refers to influenza viruses found chiefly in birds but that can also infect humans or other animals. In some instances, avian influenza viruses may be transmitted or spread from one human to another. An avian influenza virus that infects humans has the potential to cause an influenza pandemic, i.e., morbidity and/or mortality in humans. A pandemic occurs when a new strain of influenza virus (a virus in which human have no natural immunity) emerges, spreading beyond individual localities, possibly around the globe, and infecting many humans at once.

As used herein, the term "chimeric protein" refers a constructs that links at least two heterologous proteins into a single macromolecule (fusion protein).

As used herein, the term "chimeric VLP" refers to a virus-like particle that comprises an avian M1 protein and at least one protein, or portion thereof, that is not from an avian influenza virus.

As used herein an "effective dose" generally refers to that amount of the VLP of the invention sufficient to induce immunity, to prevent and/or ameliorate influenza virus infection or to reduce at least one symptom of influenza infection and/or to enhance the efficacy of another dose of a VLP. An effective dose may refer to the amount of the VLP sufficient to delay or minimize the onset of an influenza infection. An effective dose may also refer to the amount of the VLP that provides a therapeutic benefit in the treatment or management of influenza infection. Further, an effective dose is the amount with respect to the VLPs of the invention alone, or in combination with other therapies, that provides a therapeutic benefit in the treatment or management of an influenza viral infection. An effective dose may also be the amount sufficient to enhance a subject's (e.g., a human's) own immune response against a subsequent exposure to influenza virus. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease or reduces the severity of symptoms.

As used herein, the term "external domain" when referring to membrane associated proteins refer to the domain(s) of the protein that are external to the cell and/or cytosol and/or a lumen. The external domain of a protein is also known as an ectodomain.

As used herein, the term "influenza VLP" refers to a VLP comprising at least one influenza protein. Said VLPs can comprise additional influenza and/or non-influenza proteins.

As used herein, the term "hemagglutinin activity" refers to the ability of HA-containing proteins, VLPs, or portions thereof to bind and agglutinate red blood cells (erythrocytes).

As used herein, the term "neuraminidase activity" refers to the enzymatic activity of NA-containing proteins, VLPs, or portions thereof to cleave sialic acid residues from substrates including proteins such as fetuin.

As use herein, the term "infectious agent" refers to microorganisms that cause an infection in a vertebrate. Usually, the organisms are viruses, bacteria, parasites and/or fungi. The term also refers to different antigenic variations of the same infectious agent.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as the influenza VLPs, or can be administered separately. Either the protein or an expression vector encoding the protein can be administered to produce an immunostimulatory effect.

As used herein the term "immunity" refers to induction of the immune system of a vertebrate wherein said induction results in the prevention, amelioration, and/or reduction of at least one symptom of an infection in said vertebrate. Immunity may also refer to a haemagglutination inhibition (HI) titer of ≥40 when VLPs of the invention have been administered to a vertebrate and said VLPs have induced an immune response against a HA of an influenza virus.

As used herein the term "non-avian influenza protein" refers to a protein that is heterologous to an avian influenza virus. Said non-avian influenza protein may be recombinantly expressed from an expression vector and may be heterologous to the expression vector.

As used herein the term "seasonal influenza virus" refers to the influenza viral strains that have been determined to be passing within the human population for a given influenza season based on epidemiological surveys conducted by National Influenza Centers worldwide. These epidemiological studies, and some isolated influenza viruses, are sent to one of four World Health Organization (WHO) reference laboratories, one of which is at the Centers for Disease Control and Prevention (CDC) in Atlanta for detailed testing. These laboratories test how well antibodies made to the current vaccine react to the circulating virus and new flu viruses. This information, along with information about flu activity, is summarized and presented to an advisory committee of the U.S. Food and Drug Administration (FDA) and at a WHO meeting. These meetings result in the selection of three viruses (two subtypes of influenza A viruses and one influenza B virus) to go into flu vaccines for the following fall and winter. The selection occurs in February for the northern hemisphere and in September for the southern hemisphere. Usually, one or two of the three virus strains in the vaccine changes each year.

As used herein, the term "vaccine" refers to a preparation of dead or weakened pathogens, or of derived antigenic determinants that is used to induce formation of antibodies or immunity against the pathogen. A vaccine is given to provide immunity to the disease, for example, influenza, which is caused by influenza viruses. In addition, the term "vaccine" also refers to a suspension or solution of an immunogen (e.g. VLP) that is administered to a vertebrate to produce protective immunity, i.e., immunity that prevents or reduces the severity of disease associated with infection. The present invention provides for vaccine compositions that are immunogenic and may provide protection against a disease associated with infection.

As use herein, the term "vertebrate" or "subject" or "patient" refers to any member of the subphylum cordata, including, without limitation, humans and other primates, including non-human primates such as chimpanzees and other apes and monkey species. Farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like are also non-limiting examples. The terms "mammals" and "animals" are included in this definition. Both adult and newborn individuals are intended to be covered.

As used herein, the term "virus-like particle" (VLP) refers to a structure that in at least one attribute resembles a virus but which has not been demonstrated to be infectious. Virus-like particle in accordance with the invention do not carry genetic information encoding for the proteins of virus-like particles. In general, virus-like particles lack a viral genome and, therefore, are noninfectious. In addition, virus-like particles can often be produced in large quantities by heterologous expression and can be easily purified.

VLPs of the Invention and Methods of Making VLPs

In general, virus like particles (VLPs) lack a viral genome and, therefore, are non-infectious. In addition, virus-like particles can often be produced by heterologous expression and can be easily purified. Most VLPs comprise at least a viral core protein. This core protein usually drives budding and release of particles from a host cell. Examples of such proteins comprise RSV M, influenza M1, HIV gag and vesicular stomatis virus (VSV) M protein. In general, VLPs are useful for preparing antigenic formulation and/or vaccines against infectious agents, e.g. influenza.

However, VLP production has not been particularly efficient. One goal of VLP production is the optimization of culture conditions to obtain the greatest possible productivity. Even incremental increases in productivity can be economically significant and can save lives. The inventors of the present invention have unexpectedly discovered that expressing avian M1 is a host cell significantly enhances production of VLPs from host cells.

Thus, the invention described herein comprises chimeric VLPs comprising an avian influenza M1 protein and at least one non-avian influenza protein (e.g. a protein from an infectious agent). In one embodiment, said non-avian influenza protein is HA and/or NA from a non-avian influenza virus. In another embodiment, said non-avian influenza protein is a seasonal influenza protein. In another embodiment, said HA or NA seasonal influenza are A/Wisconsin/67/2005 and/or A/Fujian/411/02. In another embodiment, said HA or NA has hemaggutinin or neuraminidase activity, respectfully. In another embodiment, said non-avian influenza protein is from a virus, bacteria, fungus and/or parasite.

Chimeric VLPs of the invention are useful for preparing vaccines and immunogenic compositions. One important feature of said chimeric VLPs is the ability to express proteins on the surface of said VLPs so that the immune system of a vertebrate can induce an immune response against said protein. However, not all proteins can be expressed on the surface of VLPs. There may be many reasons why certain proteins are not expressed, or poorly expressed, on the surface of VLPs. One reason is that said protein is not directed to the membrane of a host cell or that said protein does not have a transmembrane domain. Sequences near the carboxyl terminus of influenza hemagglutinin may be important for incorporation of HA into the lipid bilayer of the mature influenza enveloped nucleocapsids and for the assembly of HA trimer interaction with the influenza core protein M1 (Ali, et al., (2000) J. Virol. 74, 8709-19). Thus, one method of overcoming the inability of expressing non-avian influenza proteins on the surface of VLPs, and/or increasing the expression of said proteins, is to fuse the cytoplasmic and/or the transmembrane domains of influenza HA and/or NA to a non-avian influenza protein thus creating a chimeric protein.

Thus, in one embodiment of the invention, said chimeric VLPs of the invention comprise at least one chimeric protein. In another embodiment, said chimeric protein comprise at least one external domain (ectodomain) of non-avian influenza HA and/or NA protein sequences fused to the transmembrane and/or cytoplasmic-terminal domains of a heterologous HA and/or NA. In another embodiment, said heterologous transmembrane and/or cytoplasmic-terminal domains HA and/or NA is from seasonal influenza and/or avian influenza virus. In another embodiment, said non-avian influenza HA and/or NA are from a seasonal influenza strain A/Wisconsin/ 67/2005 and HA and/or NA transmembrane and/or cytoplasmic-terminal domains are from an avian influenza strain. In another embodiment, said non-avian influenza HA and/or NA are from influenza strain A/Fujian/411/02 and HA and/or NA transmembrane and/or cytoplasmic-terminal domains are from an avian influenza strain. Said HA and/or NA transmembrane and/or cytoplasmic-terminal domains from avian influenza can be derived from the group consisting of influenza virus H9N2 and/or influenza virus H5N1.

Said HA and/or NA from H9N2 influenza strain can be isolated from any one of the influenza virus from the group consisting of A/quail/Hong Kong/G1/97, A/Hong Kong/ 1073/99, A/Hong Kong/2108/03, Duck/HK/Y280/97, CK/HK/G9/97, Gf/HK/SSP607/03, Ph/HK/CSW1323/03, WDk/ST/4808/01, CK/HK/NT142/03, CK/HK/WF126/03, SCk/HK/WF285/03, CK/HK/YU463/03, CK/HK/YU577/ 03, SCk/HK/YU663/03, Ck/HK/CSW161/03, and GF/HK/ NT101/03. In one embodiment, said H9N2 influenza strain is A/Hong Kong/1073/99. In another embodiment, said HA and/or NA from influenza strain H5N1 can be from Glade 1 and/or Glade 2. In another embodiment, said H5N1 is from Glade 1. In another embodiment, said H5N1 is from Glade 2. In another embodiment, said H5N1 is selected from the group consisting of A/Vietnam/1194/04, A/Vietnam/1203/04, A/Hongkong/213/03, A/Indonesia/2/2005, A/Bar headed goose/Quinghai/1A/2005, A/Anhui/1/2005, and A/Indonesia/5/05. In another embodiment, said H5N1 strain is A/Indonesia/5/05.

Chimeric VLPs of the invention comprise an avian influenza M1 protein. Said M1 protein can be derived from influenza strain H9N2 or H5N1. Said H9N2 influenza M1 can be isolated from any one of the influenza virus from the group consisting of A/quail/Hong Kong/G1/97, A/Hong Kong/ 1073/99, A/Hong Kong/2108/03, Duck/HK/Y280/97, CK/HK/G9/97, Gf/HK/SSP607/03, Ph/HK/CSW1323/03, WDk/ST/4808/01, CK/HK/NT142/03, CK/HK/WF126/03, SCk/HK/WF285/03, CK/HK/YU463/03, CK/HK/YU577/ 03, SCk/HK/YU663/03, Ck/HK/CSW161/03, and GF/HK/ NT101/03. In one embodiment, said H9N2 influenza strain is A/Hong Kong/1073/99. In another embodiment, said M1 can be from influenza strain H5N1. In another embodiment, said H5N1 is selected from the group consisting of A/Vietnam/ 1194/04, A/Vietnam/1203/04, A/Hongkong/213/03, A/Indonesia/2/2005, A/Bar headed goose/Quinghai/1A/2005, A/Anhui/1/2005, and A/Indonesia/5/05. In another embodiment, said H5N1 strain is A/Indonesia/5/05.

In another embodiment of the invention, said chimeric VLPs of the invention comprise chimeric proteins from influenza B viruses. In one embodiment, said chimeric proteins comprise external domains of influenza B HA and/or NA protein sequences fused to the transmembrane and/or cytoplasmic-terminal domains of a heterologous HA and/or NA cytoplasmic and/or transmembrane region. In another embodiment, said heterologous HA and/or NA is from seasonal influenza A/Wisconsin/67/2005 and/or A/Fujian/411/ 02 and/or avian influenza A/Indonesia/5/05. In another embodiment, said influenza B viruses are from B/Shanghai/ 361/2002 and/or B/Hong Kong/330/2001.

In another embodiment of the invention, chimeric VLPs of the invention comprise an avian M1 with a protein from another infectious agent (non-avian influenza protein). Said protein from another infectious agent can be a type 1 and/or a type 2 protein. A type I protein has a C-terminus located in the cytosol (the transmembrane domain is located near the C-terminus), whereas a type II protein has an N-terminus that is located in the cytosol (the transmembrane domain is located near the N-terminus). In another embodiment, said protein may comprise epitopes that can induce an immune response against said protein when administered to a vertebrate. In another embodiment, said protein can associate with avian influenza M1 directly or indirectly. In another embodiment, said protein is expressed on the surface of the VLP. In another embodiment, said protein, or portion thereof, can be fused to a heterologous protein creating a chimeric protein. For example, the external domains of proteins from infective agents, such as non-avian influenza virus, coronavirus, VZV, Dengue, or yellow fever and/or other agents can be used to generate chimeric proteins by fusing said proteins from infective agents with a protein that associates with avian influenza M1. In one embodiment, said protein that associates with avian influenza M1 is an influenza protein. In another embodiment, said protein that associates with avian M1 is a HA and/or NA from influenza. In another embodiment, said HA and/or NA is from a seasonal influenza virus. In another embodiment, said HA and/or NA is from an avian influenza virus. In another embodiment, said avian influenza virus is H5N1. In another embodiment, said H5N1 strain is A/Indonesia/5/05.

In another embodiment, the invention comprises a VLP comprising a chimeric protein comprising the transmembrane domain and/or cytoplasmic tail of influenza HA and/or influenza NA fused to a protein from an infective agent. In another embodiment, the transmembrane domain and/or cytoplasmic tail of the HA and/or NA protein extends from the N or C-terminus to approximately 0, 1, 2, 3, 4, 5, 6, 7, 8, 9, 10, 11, 12, 13, 14, 15, 16, 17, 18, 19, 20 to about 50 amino acids past the transmembrane domain and is fused to said protein from another infectious agent. In another embodiment, the portion of the protein from another infectious agent that comprises the cytoplasmic and the transmembrane domain is replaced with a cytoplasmic and/or transmembrane domain from an influenza protein (i.e. avian and/or seasonal influenza NA and/or HA). In another embodiment, said seasonal influenza HA and/or NA are from influenza strain A/Wisconsin/67/2005 and/or A/Fujian/411/02 and/or avian influenza A/Indonesia/5/05. In another embodiment, said M1 is from an avian influenza strain H5N1. In another embodiment, said M1 is from influenza strain A/Indonesia/5/05. In another embodiment, said M1 is from influenza strain H9N2. In another embodiment, said M1 is from influenza strain A/Hong Kong/1073/99. In another embodiment, the transmembrane domain and/or cytoplasmic tail of A/Wisconsin/67/2005 HA and/or NA is fused to a protein from an infectious agent. In another embodiment, the transmembrane domain and/or cytoplasmic tail of A/Fujian/411/02 HA and/or NA is fused to a protein from an infectious agent. In another embodiment, the transmembrane domain and/or cytoplasmic tail of A/Indonesia/5/05 HA and/or NA is fused to a protein from an infectious agent.

In another embodiment, the transmembrane domain and/or cytoplasmic tail of influenza HA and/or influenza NA fused to a protein from an infective agent comprises a spacer sequence between the protein segments. Said space sequences can be any amino acid not in the protein. This spacer sequence may be important for expressing said protein from an infective agent on the surface of the VLP. Examples of spacer sequences include a poly-G amino acids. Said spacer can be from 1 to about 100 amino acids long.

In another embodiment of the invention, said VLPs comprise more than one protein from an infectious agent. In this embodiment, said VLPs are multivariant VLPs capable of inducing an immune response to several proteins from infectious agents. In one embodiment said VLPs comprise proteins from at least two different influenza viruses. For example said multivariant VLPs can comprise a HA and/or NA from a seasonal influenza virus A and/or B and/or from an avian influenza virus. This embodiment also comprises the presentation of HA and/or NA of the three influenza viruses (two subtypes of influenza A viruses and one influenza B virus) that are chosen by WHO and the CDC (see above) to be in the flu vaccines for the fall and winter in a single VLP. In another embodiment, said multivariant VLPs comprise proteins from several viruses, bacteria and/or parasites. For example, said VLPs comprise proteins from influenza and RSV, influenza, RSV and parainfluenza. In another embodiment, said proteins are chimeric proteins wherein each protein comprises the HA and/or NA from an influenza virus. In another embodiment, said multivalent VLPs comprise an avian influenza M1 protein. In another embodiment, said avian influenza is A/Indonesia/5/05.

In another embodiment, said chimeric proteins comprise a fusion between the influenza HA with the protein, or a portion thereof, from an infectious agent. In another embodiment, said chimeric proteins comprise a fusion between the proteins, or a portion thereof, of two infectious agents or antigenic variations of the same agent. Said fusion protein will comprise antigenic agents from each protein from said infectious agent. In another embodiment, said chimeric protein comprises an amino acid linker between the proteins. An example of this embodiment is a fusion between the influenza HA and the RSV F protein. An example of this embodiment is a fusion between the influenza HA and the RSV F1 protein (e.g. SEQ ID NO 12). In another embodiment, said chimeric protein comprises the HA and/or NA transmembrane and/or cytoplasmic domain from an avian influenza virus. In another embodiment, said multivalent VLPs comprise an avian influenza M1 protein. In another embodiment, said avian influenza is A/Indonesia/5/05.

In another embodiment of the invention, the chimeric genes (as describe above), which may be codon optimized, are synthesized and cloned through a series of steps into a bacmid construct followed by rescue of recombinant baculovirus by plaque isolation and expression analyses. The VLPs for each of these targets can then be rescued by co-infection with the use of two recombinant baculoviruses (1) expressing the avian M1, and (2) expressing the chimeric protein from an infectious agent (e.g. VZV, RSV, Dengue, yellow fever) with cytoplasmic and/or transmembrane domain from HA and/or NA from a seasonal and/or avian influenza virus. In another embodiment, the VLPs of the invention can be rescued by infection with the use of a recombinant baculovirus expressing the avian M1 and the chimeric protein from an infectious agent (e.g. VZV, RSV, Dengue, yellow fever) with cytoplasmic and transmembrane domain from influenza HA and/or NA.

Infectious agents can be viruses, bacteria, fungi and/or parasites. A protein that may be expressed on the surface of chimeric VLPs of the invention can be derived from viruses, bacteria, fungi and/or parasites. In other embodiments, the proteins expressed on the surface of said chimeric VLPs may be tumor or cancer antigens. The proteins derived from viruses, bacteria, fungi and/or parasites can induce an immune response (cellular and/or humoral) in a vertebrate that which will prevent, treat, manage and/or ameliorate an infectious disease in said vertebrate.

Non-limiting examples of viruses from which said infectious agent proteins can be derived from are the following: coronavirus (e.g. the agent that causes SARS), hepatitis viruses A, B, C, D & E3, human immunodeficiency virus (HIV), herpes viruses 1, 2, 6 & 7, cytomegalovirus, varicella zoster, papilloma virus, Epstein Barr virus, parainfluenza viruses, respiratory syncytial virus (RSV), human metapneumovirus, adenoviruses, bunya viruses (e.g. hanta virus), coxsakie viruses, picoma viruses, rotaviruses, rhinoviruses, rubella virus, mumps virus, measles virus, Rubella virus, polio virus (multiple types), adeno virus (multiple types), parainfluenza virus (multiple types), avian influenza (various types), shipping fever virus, Western and Eastern equine encephalomyelitis, Japanese encephalomyelitis, fowl pox, rabies virus, slow brain viruses, rous sarcoma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), Togaviridae (e.g., Rubi virus), Newcastle disease virus, West Nile fever virus, Tick borne encephalitis, yellow fever, chikungunya virus, and dengue virus (all serotypes).

In another embodiment, the specific proteins from viruses may comprise: HA and/or NA from influenza virus (including avian), S protein from coronavirus, gp160, gp140 and/or gp41 from HIV, gp I to IV and Vp from varicella zoster, E and preM/M from yellow fever virus, Dengue (all serotypes) or any flavivirus. Also included are any proteins from a virus that can induce an immune response (cellular and/or humoral) in a vertebrate that can prevent, treat, manage and/or ameliorate an infectious disease in said vertebrate.

Non-limiting examples of bacteria from which said infectious agent proteins can be derived from are the following: *B. pertussis, Leptospira pomona, S. paratyphi* A and B, *C. diphtheriae, C. tetani, C. botulinum, C. perfringens, C. feseri* and other gas gangrene bacteria, *B. anthracis, P. pestis, P. multocida, Neisseria meningitidis, N. gonorrheae, Hemophihis influenzae, Actinomyces* (e.g., *Norcardia*), *Acinetobacter,* Bacillaceae (e.g., *Bacillus anthracis*), *Bacteroides* (e.g., *Bacteroides fragilis*), Blastomycosis, *Bordetella, Borrelia* (e.g., *Borrelia burgdorferi*), *Brucella, Campylobacter, Chlamydia, Coccidioides, Corynebacterium* (e.g., *Corynebacterium diptheriae*), *E. coli* (e.g., Enterotoxigenic *E. coli* and Enterohemorrhagic *E. coli*), *Enterobacter* (e.g. *Enterobacter aerogenes*), Enterobacteriaceae (*Klebsiella, Salmonella* (e.g., *Salmonella typhi, Salmonella enteritidis, Serratia, Yersinia, Shigella*), *Erysipelothrix, Haemophilus* (e.g., *Haemophilia influenza* type B), *Helicobacter, Legionella* (e.g., *Legionella pneumophila*), *Leptospira, Listeria* (e.g., *Listeria monocytogenes*), *Mycoplasma, Mycobacterium* (e.g., *Mycobacterium leprae* and *Mycobacterium tuberculosis*), *Vibrio* (e.g., *Vibrio cholerae*), Pasteurellacea, *Proteus, Pseudomonas* (e.g., *Pseudomonas aeruginosa*), Rickettsiaceae, Spirochetes (e.g., *Treponema* spp., *Leptospira* spp., *Borrelia* spp.), *Shigella* spp., *Meningiococcus, Pneumococcus* and *Streptococcus* (e.g., *Streptococcus pneumoniae* and Groups A, B, and C Streptococci), Ureaplasmas. *Treponema pollidum, Staphylococcus aureus, Pasteurella haemolytica, Corynebacterium diptheriae* toxoid, Meningococcal polysaccharide, *Bordetella pertusis, Streptococcus pneumoniae, Clostridium tetani* toxoid, and *Mycobacterium bovis.*

Non-limiting examples of parasites from which said infectious agent proteins can be derived from are the following: leishmaniasis (*Leishmania tropica mexicana, Leishmania tropica, Leishmania major, Leishmania aethiopica, Leishmania braziliensis, Leishmania donovani, Leishmania infantum, Leishmania chagasi*), trypanosomiasis (*Trypanosoma brucei gambiense, Trypanosoma brucei rhodesiense*), toxoplasmosis (*Toxoplasma gondii*), schistosomiasis (*Schistosoma haematobium, Schistosoma japonicum, Schistosoma mansoni, Schistosoma mekongi, Schistosoma intercalatum*), malaria (*Plasmodium virax, Plasmodium falciparum, Plasmodium malariae* and *Plasmodium ovale*) Amebiasis (*Entamoeba histolytica*), Babesiosis (*Babesiosis microti*), Cryptosporidiosis (*Cryptosporidium parvum*), Dientamoebiasis (*Dientamoeba fragilis*), Giardiasis (*Giardia lamblia*), Helminthiasis and Trichomonas (*Thichomonas vaginalis*).

Non-limiting examples of fungi from which said glycoproteins can be derived are from the following: *Absidia* (e.g. *Absidia corymbifera*), *Ajellomyces* (e.g. *Ajellomyces capsulatus, Ajellomyces dermatitidis*), *Arthroderma* (e.g. *Arthroderma benhamiae, Arthroderma falvum, Arthroderma gypseum, Arthroderma incurvalum, Arthroderma otae, Arthroderma vanbreuseghemii*), *Aspergillus* (e.g. *Aspergillus fumigatus, Aspergillus Niger*), *Candida* (e.g. *Candida albicans, Candida albicans* var. *stellatoidea, Candida dublinensis, Candida glabrata, Candida guilliermondii* (*Pichia guilliermondii*), *Candida krusei* (*Issatschenkia orientalis*), *Candida parapsilosis, Candida pelliculosa* (*Pichia anomala*), *Candida tropicalis*), *Coccidioides* (e.g. *Coccidioides immitis*), *Cryptococcus* (e.g. *Cryptococcus neoformans* (*Filobasidiella neoformans*), *Histoplasma* (e.g. *Histoplasma capsulatum* (*Ajellomyces capsulatus*), *Microsporum* (e.g. *Microsporum canis* (*Arthroderma otae*), *Microsporum fulvum* (*Arthroderma fulvum*), *Microsporum gypseum*, Genus *Pichia* (e.g. *Pichia anomala, Pichia guilliermondii*), *Pneumocystis* (e.g. *Pneumocystis jirovecii*), *Cryptosporidium, Malassezia furfur,* Paracoccidiodes.

The above lists are meant to be illustrative and by no means are meant to limit the invention to those particular bacterial, viral or parasitic organisms.

The invention also encompasses variants of the said proteins expressed on or in the chimeric VLPs of the invention. The variants may contain alterations in the amino acid sequences of the constituent proteins. The term "variant" with respect to a protein refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Natural variants can occur due to mutations in the proteins. These mutations may lead to antigenic variability within individual groups of infectious agents, for example influenza. Thus, a person infected with an influenza strain develops antibody against that virus, as newer virus strains appear, the antibodies against the older strains no longer recognize the newer virus and reinfection can occur. The invention encompasses all antigenic and genetic variability of proteins from infectious agents for making chimeric VLPs.

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology. F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating HA, NA and/or proteins from infectious agents, etc. Thus, the invention also encompasses using known methods of protein engineering and recombinant DNA technology to improve or alter the characteristics of the proteins expressed on or in the VLPs of the invention. Various types of mutagenesis can be used to produce and/or isolate variant nucleic acids that encode for protein molecules and/or to further modify/mutate the proteins in or on the VLPs of the invention. They include but are not limited to site-directed, random point mutagenesis, homologous recombination (DNA shuffling), mutagenesis using uracil containing templates, oligonucleotide-directed mutagenesis, phosphorothioate-modified fled DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The invention further comprises protein variants which show substantial biological activity, e.g., able to elicit an effective antibody response when expressed on or in VLPs of the invention. Such variants include deletions, insertions, inversions, repeats, and substitutions selected according to general rules known in the art so as have little effect on activity.

Methods of cloning said proteins are known in the art. For example, the gene encoding a specific virus protein can be isolated by RT-PCR from polyadenylated mRNA extracted from cells which had been infected with a virus (DNA or RNA virus) or PCR from cells which had been infected with a DNA virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode proteins, including chimeric molecules, cloned into an expression vector that can be expressed in a cell that induces the formation of VLPs of the invention. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, said nucleotides encode for a non-avian influenza protein and/or chimeric protein (as discussed above). In another embodiment, said vector comprises nucleotides that encode for a non-avian influenza protein and/or chimeric protein and an avian influenza M1. In another embodiment, said vector comprises nucleotides that encode a chimeric protein comprising the cytoplasmic and/or the transmembrane domain of HA and/or NA from avian and/or seasonal influenza protein. In another embodiment, said seasonal influenza HA and/or NA are from influenza strain A/Wisconsin/67/2005 and said avian influenza HA and/or NA are from influenza strain A/Indonesia/5/05. In another embodiment, said vector comprises nucleotides that encode M1 from influenza strain A/Indonesia/5/05 and a chimeric protein comprising the A/Wisconsin/67/2005 (seasonal influenza) cytoplasmic and/or the transmembrane from HA and/or NA. In another embodiment, said vector comprises nucleotides that encode M1 from influenza strain A/Indonesia/5/05 and a chimeric protein comprising the A/Indonesia/5/05 (avian influenza) cytoplasmic and/or the transmembrane from HA and/or NA.

In some embodiments, said proteins may comprise, mutations containing alterations that produce silent substitutions, additions, or deletions, but do not alter the properties or activities of the encoded protein or how the proteins are made. Nucleotide variants can be produced for a variety of reasons, e.g., to optimize codon expression for a particular host (change codons in the human mRNA to those preferred by insect cells such as Sf9 cells). See U.S. patent publication 2005/0118191, herein incorporated by reference in its entirety for all purposes.

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the influenza proteins (including chimeric proteins) can be cloned. A person with skill in the art understands that additional methods are available and are possible.

The invention also provides for constructs and/or vectors that comprise nucleotides that encode for avian M1 and non-avian influenza proteins and/or chimeric proteins (as described above). The constructs and/or vectors that comprise avian M1 and non-avian influenza proteins and/or chimeric proteins, should be operatively linked to an appropriate promoter, such as the AcMNPV polyhedrin promoter (or other baculovirus), phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan.

Next, the recombinant constructs mentioned above could be used to transfect, infect, or transform and can express avian M1 and a non-avian influenza protein and/or chimeric proteins, into eukaryotic cells and/or prokaryotic cells. Thus, the invention provides for host cells that comprise a vector (or vectors) that contain nucleic acids which code for avian M1 and chimeric proteins, and permit the expression of said constructs in said host cell under conditions which allow the formation of VLPs.

Among eukaryotic host cells are yeast, insect, avian, plant, *C. elegans* (or nematode) and mammalian host cells. Non limiting examples of insect cells are, *Spodoptera frugiperda* (Sf) cells, e.g. Sf9, Sf21, *Trichoplusia ni* cells, e.g. High Five cells, and *Drosophila* S2 cells. Examples of fungi (including yeast) host cells are *S. cerevisiae, Kluyveromyces lactis* (*K. lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO)

cells, human embryonic kidney (HEK) cells, and African green monkey cells, CV1 cells, HeLa cells, MDCK cells, Vero and Hep-2 cells. *Xenopus laevis* oocytes, or other cells of amphibian origin, may also be used. Prokaryotic host cells include bacterial cells, for example, *E. coli, B. subtilis*, and mycobacteria.

Vectors, e.g., vectors comprising polynucleotides of avian M1 and non-avian influenza proteins and/or chimeric proteins, can be transfected into host cells according to methods well known in the art. For example, introducing nucleic acids into eukaryotic cells can be by calcium phosphate co-precipitation, electroporation, microinjection, lipofection, and transfection employing polyamine transfection reagents. In one embodiment, said vector is a recombinant baculovirus. In another embodiment, said recombinant baculovirus is transfected into a eukaryotic cell. In a preferred embodiment, said cell is an insect cell. In another embodiment, said insect cell is a Sf9 cell.

In another embodiment, said vector and/or host cell comprise nucleotides that encode avian M1 and non-avian influenza proteins and/or chimeric proteins. In another embodiment, said vector and/or host cell consists essentially of avian M1 and non-avian influenza proteins and/or chimeric proteins. In a further embodiment, said vector and/or host cell consists of avian M1 and non-avian influenza proteins and/or chimeric proteins. These vector and/or host cell contain avian M1 and non-avian influenza proteins and/or chimeric proteins, and may contain additional markers, such as an origin of replication, selection markers, etc.

The invention also provides for constructs and methods that will further increase the efficiency of VLPs production. For example, the addition of leader sequences to the avian M1 and non-avian influenza proteins and/or chimeric proteins, can improve the efficiency of protein transporting within the cell. For example, a heterologous signal sequence can be fused to avian M1 and non-avian influenza proteins and/or chimeric proteins. In one embodiment, the signal sequence can be derived from the gene of an insect preprotein and fused to avian M1 and non-avian influenza proteins and/or chimeric proteins. In another embodiment, the signal peptide is the chitinase signal sequence, which works efficiently in baculovirus expression systems.

The invention also comprises a method of increasing the efficiency of producing chimeric VLPs comprising expressing an avian influenza M1 and at least one non-avian influenza protein in a host cell. In one embodiment, said VLP comprises HA and/or NA from a non-avian influenza virus. In another embodiment, said non-avian influenza protein is a seasonal influenza protein. In another embodiment, said HA or NA have hemaggutinin and neuraminidase activity, respectfully. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of the avian HA and/or NA. In another embodiment, said non-avian influenza HA and/or NA are from influenza strain A/Wisconsin/67/2005 and said avian influenza HA and/or NA are from influenza strain A/Indonesia/5/05. In another embodiment, said M1 is from influenza strain A/Indonesia/5/05. In another embodiment, said HA and/or NA is from influenza strain A/Wisconsin/67/2005.

In another embodiment of the invention, the increase in VLP production, for chimeric or non-chimeric VLPs, is about 2 fold, about 4 fold, about 8 fold, about 16 fold, about 20 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, or more when compared to VLP production comprising a non-avian influenza M1 protein under similar conditions, for instance seasonal influenza M1. In one embodiment, the efficiency of producing influenza VLPs is increase by about 10%, about 20% about 30%, about 40%, about 50% about 60%, about 70% about 80%, about 90%, about 100%, about 150%, about 200%, about 250%, about 300%, about 350%, about 400%, about 450%, about 500%, about 550%, about 600%, about 650%, about 700%, about 750%, about 800% about 850% about 900% about 950% about 1000% when compared to VLP production comprising a non-avian influenza M1 protein under similar conditions. A preferred M1 is from A/indonesia/5/05 (SEQ ID NO. 3).

The invention also provides for methods of producing VLPs of the invention, said methods comprising expressing an avian M1 and a non-avian influenza protein (e.g. seasonal HA and/or NA) under conditions that allow the formation of VLPs. Depending on the expression system and host cell selected, VLPs are produced by growing host cells transformed by an expression vector under conditions whereby the recombinant proteins (e.g. avian M1 and a non-avian influenza protein) are expressed and VLPs are formed. The selection of the appropriate growth conditions is within the skill or a person with skill of one of ordinary skill in the art.

Methods to grow cells engineered to produce VLPs of the invention include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, said bioreactor is a stainless steel chamber. In another embodiment, said bioreactor is a pre-sterilized plastic bag (e.g. Cellbag®, Wave Biotech, Bridgewater, N.J.). In other embodiment, said pre-sterilized plastic bags are about 50 L to 1000 L bags.

VLPs are then isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how VLPs of the invention can be made, isolated and purified. Usually VLPs are produced from recombinant cell lines engineered to create a VLP when said cells are grown in cell culture (see above). A person of skill in the art would understand that there are additional methods that can be utilized to make and purify VLPs of the invention, thus the invention is not limited to the method described.

Production of VLPs of the invention can start by seeding Sf9 cells (non-infected) into shaker flasks, allowing the cells to expand and scaling up as the cells grow and multiply (for example from a 125-ml flask to a 50 L Wave bag). The medium used to grow the cell is formulated for the appropriate cell line (preferably serum free media, e.g. insect medium ExCell-420, JRH). Next, said cells are infected with recombinant baculovirus at the most efficient multiplicity of infection (e.g. from about 1 to about 3 plaque forming units per cell). Once infection has occurred, the avian influenza M1 and at least one avian influenza heterologous protein are expressed from the virus genome, self assemble into VLPs and are secreted from the cells approximately 24 to 72 hours post infection. Usually, infection is most efficient when the cells are in mid-log phase of growth (4-8×10$^6$ cells/ml) and are at least about 90% viable.

VLPs of the invention can be harvested approximately 48 to 96 hours post infection, when the levels of VLPs in the cell culture medium are near the maximum but before extensive cell lysis. The Sf9 cell density and viability at the time of harvest can be about 0.5×10$^6$ cells/ml to about 1.5×10$^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation. The removal of cell and cellular debris from the cell culture medium containing VLPs of the invention can be accomplished by tangential flow filtration (TFF) with a single use, pre-sterilized hollow fiber 0.5 or 1.00 μm filter cartridge or a similar device.

Next, VLPs in the clarified culture medium can be concentrated by ultrafiltration using a disposable, pre-sterilized 500, 000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be further purified on a 20% to 60% discontinuous sucrose gradient in pH 7.2 PBS buffer with 0.5 M NaCl by centrifugation at 6,500×g for 18 hours at about 4° C. to about 10° C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or β-propyl lactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25° C. to about 27° C. The baculovirus can also be inactivated by incubating the sample containing the VLPs at 0.05% BPL at 4° C. for 3 days, then at 37° C. for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

Expansion and production of baculovirus expression vectors and infection of cells with recombinant baculovirus to produce recombinant influenza VLPs can be accomplished in insect cells, for example Sf9 insect cells as previously described. In a preferred embodiment, the cells are Sf9 infected with recombinant baculovirus engineered to produce VLPs of the invention.

Pharmaceutical or Vaccine Formulations and Administration

The invention comprises an antigenic formulation comprising a chimeric VLP comprising an avian influenza M1 protein and at least one non-avian influenza protein. In one embodiment, said VLP comprises HA and/or NA from a non-avian influenza virus. In another embodiment, said HA or NA have hemaggutinin and neuraminidase activity, respectfully. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of the avian HA and/or NA cytoplasmic region. In another embodiment, said non-avian influenza HA and/or NA are from influenza strain A/Wisconsin/67/2005 and said avian influenza HA and/or NA are from influenza strain A/Indonesia/5/05. In another embodiment, said M1 is from influenza strain A/Indonesia/5/05. In another embodiment, said HA and/or NA is from influenza strain A/Wisconsin/67/2005.

The invention comprises a vaccine comprising a chimeric VLP comprising an avian influenza M1 protein and at least one non-avian influenza protein. In one embodiment, said VLP comprises HA and/or NA from a non-avian influenza virus. In another embodiment, said HA or NA have hemaggutinin and neuraminidase activity, respectfully. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of the avian HA and/or NA cytoplasmic region. In another embodiment, said non-avian influenza HA and/or NA are from influenza strain A/Wisconsin/67/2005 and said avian influenza HA and/or NA are from influenza strain A/Indonesia/5/05. In another embodiment, said M1 is from influenza strain A/Indonesia/5/05. In another embodiment, said HA and/or NA is from influenza strain A/Wisconsin/67/2005.

The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a VLP of the invention. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

The invention comprises an antigenic formulation comprising a chimeric VLP comprising an avian influenza M1 protein and at least one non-avian influenza protein. In one embodiment, said VLP comprises HA and/or NA from a non-avian influenza virus. In another embodiment, said HA or NA have hemaggutinin and neuraminidase activity, respectfully. In another embodiment, said HA and/or NA are chimeric proteins. In another embodiment, said chimeric proteins comprise external domains of non-avian influenza HA and/or NA protein sequences fused to the transmembrane and/or Cytoplasmic-terminal domains of the avian HA and/or NA cytoplasmic region. In another embodiment, said non-avian influenza HA and/or NA are from influenza strain A/Wisconsin/67/2005 and said avian influenza HA and/or NA are from influenza strain A/Indonesia/5/05. In another embodiment, said M1 is from influenza strain A/Indonesia/5/05. In another embodiment, said HA and/or NA is from influenza strain A/Wisconsin/67/2005.

The invention comprises a vaccine comprising a chimeric VLP comprising an avian influenza M1 protein and at least one non-avian influenza protein. In one embodiment, said VLP comprises HA and/or NA from a non-avian influenza virus. In another embodiment, said HA or NA have hemaggutinin and neuraminidase activity, respectfully. In another embodiment, said HA and/or NA are chimeric proteins. In another embodiment, said chimeric proteins comprise external domains of non-avian influenza HA and/or NA protein sequences fused to the transmembrane and/or cytoplasmic-terminal domains of the avian HA and/or NA cytoplasmic region. In another embodiment, said non-avian influenza HA and/or NA are from influenza strain A/Wisconsin/67/2005 and said avian influenza HA and/or NA are from influenza strain A/Indonesia/5/05. In another embodiment, said M1 is from influenza strain A/Indonesia/5/05. In another embodiment, said HA and/or NA is from influenza strain A/Wisconsin/67/2005.

Said formulations of the invention comprise a formulation comprising VLPs comprising an avian M1 protein and at least one protein from a non-avian influenza protein (e.g. a protein from an infectious agent described above) and a pharmaceutically acceptable carrier or excipient. Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In another embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The invention also provides for a pharmaceutical pack or kit comprising one or more containers filled with one or more of the ingredients of the vaccine formulations of the invention. In one embodiment, the kit comprises two containers, one containing VLPs and the other containing an adjuvant. In another embodiment, the kit comprises two containers, one containing freeze dried VLPs and the other containing a solution to resuspend said VLPs. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the VLP formulation be packaged in a hermetically sealed container such as an ampoule or sachette indicating the quantity of composition. In one embodiment, the VLP composition is supplied as a liquid, in another embodiment, as a dry sterilized lyophilized powder or water free concentrate in a hermetically sealed container and can be reconstituted, e.g., with water or saline to the appropriate concentration for administration to a subject. In one embodiment, said container comprises at least about 50 µg/ml, more preferably at least about 100 µg/ml, at least about 200 µg/ml, at least 500 µg/ml, or at least 1 mg/ml of an antigen associated with VLPs of the invention.

In an alternative embodiment, the VLP composition is supplied in liquid form in a hermetically sealed container indicating the quantity and concentration of the VLP composition. The liquid form of the VLP composition is supplied in a hermetically sealed container at least about 50 µg/ml, more preferably at least about 100 µg/ml, at least about 200 µg/ml, at least 500 µg/ml, or at least 1 mg/ml of an antigen associated with VLPs of the invention.

Generally, VLPs of the invention are administered in an effective amount or quantity (as defined above) sufficient to stimulate an immune response against one or more infectious agents. Preferably, administration of the VLP of the invention elicits immunity against an infectious agent. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in an immune response, intranasal administration confers the added benefit of eliciting mucosal immunity at the site of entry of many viruses, including RSV and influenza.

Thus, the invention also comprises a method of formulating a vaccine or antigenic composition that induces immunity to an infection or at least one symptom thereof to a mammal, comprising adding to said formulation an effective dose of VLPs of the invention.

Methods of administering a composition comprising VLPs (vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition comprising VLPs of the invention may induce an antibody or other immune response that is substantially higher than other routes of administration. In another embodiment, intranasal or other mucosal routes of administration of a composition comprising VLPs of the invention may induce an antibody or other immune response that will induce cross protection against other strains or organisms that cause infection. For example, a VLP comprising influenza protein, when administered to a vertebrate, can induce cross protection against several influenza strains. Administration can be systemic or local.

In yet another embodiment, the vaccine and/or antigenic formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccines and/or antigenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration. In another embodiment, said VLPs of the invention can be administered as part of a combination therapy. For example, VLPs of the invention can be formulated with other immunogenic compositions, antivirals and/or antibiotics.

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the efficacy of vaccines include the guinea pig, hamster, ferrets, chinchilla, mouse and cotton rat. Most animals are not natural hosts to infectious agents but can still serve in studies of various aspects of the disease. For example, any of the above animals can be dosed with a vaccine candidate, e.g. VLPs of the invention, to partially characterize the immune response induced, and/or to determine if any neutralizing antibodies have been produced. For example, many studies have been conducted in the mouse model because mice are small size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients ($2^{nd}$ Edition)," herein incorporated by reference in its entirety for all purposes, is envisioned within the scope of this invention.

Exemplary, adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MF-59, Novasomes®, MHC antigens may also be used.

In one embodiment of the invention, the adjuvant is a paucilamellar lipid vesicle having about two to ten bilayers arranged in the form of substantially spherical shells separated by aqueous layers surrounding a large amorphous central cavity free of lipid bilayers. Paucilamellar lipid vesicles may act to stimulate the immune response several ways, as non-specific stimulators, as carriers for the antigen, as carriers of additional adjuvants, and combinations thereof. Paucilamellar lipid vesicles act as non-specific immune stimulators when, for example, a vaccine is prepared by intermixing the antigen with the preformed vesicles such that the antigen remains extracellular to the vesicles. By encapsulating an antigen within the central cavity of the vesicle, the vesicle acts both as an immune stimulator and as a carrier for the antigen. In another embodiment, the vesicles are primarily made of nonphospholipid vesicles. In another embodiment, the vesicles are Novasomes. Novasomes® are paucilamellar nonphospholipid vesicles ranging from about 100 nm to about 500 nm. They comprise Brij 72, cholesterol, oleic acid and squalene. Novasomes have been shown to be an effective adjuvant for influenza antigens (see, U.S. Pat. Nos. 5,629,021, 6,387,373, and 4,911,928, herein incorporated by reference in their entireties for all purposes).

Another method of inducing an immune response can be accomplished by formulating the VLPs of the invention with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3. IL-4, IL-12, IL-13); growth factors (e.g., granulocyte-macrophage (GM)-colony stimulating actor (CSF)); and other immunostimulatory molecules, such as macrophage inflammatory factor, Flt3 ligand, B7.1; B7.2, etc. The immunostimulatory molecules can be administered in the same formulation as the RSV VLPs, or can be administered separately. Either the protein or an expression vector encoding the protein can be administered to produce an immunostimulatory effect. Thus in one embodiment, the invention comprises antigentic and vaccine formulations comprising an adjuvant and/or an immune stimulator.

Thus, one embodiment of the invention comprises a formulation comprising a chimeric VLP comprising an avian M1 and at least one non-avian influenza protein (or at least one protein from an infectious agent) and adjuvant and/or an immune stimulator. In another embodiment, said adjuvant are Novasomes. In another embodiment, said formulation is suitable for human administration. In another embodiment, the formulation is administered to a vertebrate orally, intradermally, intranasally, intramuscularly, intraperitoneally, intravenously or subcutaneously. In another embodiment, different chimeric VLPs are blended together to create a multivalent formulation. These VLPs may comprise VLPs HA and/or NA from different strains of influenza virus (e.g. influenza A and/or influenza B) or protein from different infectious agents (e.g. RSV, coronavirus, HIV).

While stimulation of immunity with a single dose is preferred, additional dosages can be administered by the same or different route to achieve the desired effect. In neonates and infants, for example, multiple administrations may be required to elicit sufficient levels of immunity. Administration can continue at intervals throughout childhood, as necessary to maintain sufficient levels of protection against infections. Similarly, adults who are particularly susceptible to repeated or serious infections, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Methods of Stimulating an Immune Response

As mentioned above, the VLPs of the invention are useful for preparing compositions that stimulate an immune response that confers immunity to infectious agents. Both mucosal and cellular immunity may contribute to immunity to infectious agents and disease. Antibodies secreted locally in the upper respiratory tract are a major factor in resistance to natural infection. Secretory immunoglobulin A (sIgA) is involved in protection of the upper respiratory tract and serum IgG in protection of the lower respiratory tract. The immune response induced by an infection protects against reinfection with the same virus or an antigenically similar viral strain. For example, influenza undergoes frequent and unpredictable changes; therefore, after natural infection, the effective period of protection provided by the host's immunity may only be a few years against the new strains of virus circulating in the community.

VLPs of the invention can induce on immunity in a vertebrate (e.g. a human) when administered to said vertebrate. The immunity results from an immune response against VLPs of the invention that protects or ameliorates infection or at least reduces a symptom of infection in said vertebrate. In some instances, if the said vertebrate is infected, said infection will be asymptomatic. The response may be not a fully protective response. In this case, if said vertebrate is infected with an infectious agent, the vertebrate will experience reduced symptoms or a shorter duration of symptoms compared to a non-immunized vertebrate.

The invention comprises a method of inducing immunity in a vertebrate comprising administering to said vertebrate a VLP comprising an avian influenza M1 protein and at least one non-avian influenza protein. In one embodiment, said immune response is a humoral immune response. In another embodiment, said immune response is a cellular immune response. In another embodiment, said non-avian influenza protein is HA and/or NA from a non-avian influenza virus. In another embodiment, said non-avian influenza protein is a seasonal influenza protein. In another embodiment, said HA or NA has hemaggutinin or neuraminidase activity, respectfully. In one embodiment, said HA and/or NA are chimeric proteins. In another embodiment, said chimeric proteins comprise external domains of non-avian influenza HA and/or NA protein sequences fused to the transmembrane and/or cytoplasmic-terminal domains of the avian HA and/or NA cytoplasmic region. In another embodiment, said non-avian influenza HA and/or NA are from influenza strain A/Wisconsin/67/2005 and said avian influenza HA and/or NA transmembrane and/or cytoplasmic-terminal domains are from influenza strain A/Indonesia/5/05. In another embodiment, said M1 is from influenza strain A/Indonesia/5/05. In another embodiment, said HA and/or NA is from influenza strain A/Wisconsin/67/2005.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as γ, μ, α, δ, or c, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. Antibodies exist as intact immunoglobulins or as a number of well-characterized fragments produced by digestion with various peptidases.

In another embodiment, the invention comprises a method of inducing a protective cellular response to an infection or at least one symptom thereof in a subject, comprising administering at least one effective dose of VLPs of the invention, wherein said VLPs comprise an avian influenza M1 protein and at least one non-avian influenza protein. Cell-mediated immunity also plays a role in recovery from infection and may prevent additional complication and contribute to long term immunity.

As mentioned above, the VLPs of the invention can prevent or reduce at least one symptom of an infection in a subject when administered to said subject. Most symptoms of most infections are well known in the art. Thus, the method of the invention comprises the prevention or reduction of at least one symptom associated with an infection. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of an infection or additional symptoms, reduced severity of symptoms or suitable assays (e.g. antibody titer and/or T-cell activation assay). The objective assessment comprises both animal and human assessments.

The invention comprises a method of preventing and/or reducing an infection or symptom thereof, comprising administering to said vertebrate a chimeric VLP comprising an avian influenza M1 protein and at least one non-avian influenza protein. In one embodiment said infection is a viral infection. In another embodiment, said viral infection is an influenza infection.

A strategy for the control of infectious diseases during an outbreak, e.g. influenza, is the universal vaccination of healthy individuals, including children. For example, vaccination with current influenza vaccines of approximately 80% of schoolchildren in a community has decreased respiratory illnesses in adults and excess deaths in the elderly (Reichert et al., 2001). This concept is known as community immunity or "herd immunity" and is thought to play an important part of protecting the community against diseases. Because vaccinated people have antibodies that neutralize and infectious agent, e.g. influenza virus, they are much less likely to transmit said agent to other people. Thus, even people who have not been vaccinated (and those whose vaccinations have become weakened or whose vaccines are not fully effective) often can be shielded by the herd immunity because vaccinated people around them are not getting sick. Herd immunity is more effective as the percentage of people vaccinated increases. It is thought that approximately 95% of the people in the community must be protected by a vaccine to achieve herd immunity. People who are not immunized increase the chance that they and others will get the disease.

Thus, the invention also comprises a method of reducing the severity of an infectious disease in a population, comprising administering a VLP comprising an avian influenza M1 protein and at least one non-avian influenza protein to enough individuals in said population in order to prevent or decrease the chance of transmission to another individual in said population. In one embodiment, said infectious disease is caused by influenza virus. The invention also encompasses a method of inducing immunity to an infectious agent to a population or a community in order to reduce the incidence of infections among immunocompromised individuals or non-vaccinated individual buy administering VLPs of the invention to a population in a community. In one embodiment, most school-aged children are immunized by administering the VLPs of the invention. In another embodiment, most healthy individuals in a community to are immunized by administering the VLPs of the invention. In another embodiment, VLPs of the invention are part of a "dynamic vaccination" strategy. Dynamic vaccination is the steady production of a low-efficacy vaccine that is related to an emerging pandemic strain, but due to an antigentic drift may not provide complete protection in a mammal (see Germann et al., 2006).

This invention is further illustrated by the following examples that should not be construed as limiting. The contents of all references, patents and published patent applications cited throughout this application, as well as the Figure and the Sequence Listing, are incorporated herein by reference for all purposes.

EXAMPLES

Example 1

Expressing Seasonal and Avian VLPs from Two Baculovirus Vectors

Seasonal and avian influenza M1 and HA proteins were cloned and expressed in a baculovirus expression system. In this example, the A/Indonesia/5/05 was cloned into a one baculovirus and the HA and/or NA was cloned in another baculovirus vector. Both viruses were co infected into Sf9 insect cells and grown under conditions that allow VLP formation. Cells comprising either seasonal HA and M1, avian HA and M1 or a combination of seasonal and avian HA and M1 were grown under conditions that allow formation of VLPs. The seasonal influenza strains used for these experiments were A/Fujian/411/2002 and A/Wisconsin/67/2005 and the avian influenza strain used was A/Indonesia/5/05.

Next, the VLPs were harvested and isolated from the supernatant by centrifugation and by a discontinuous sucrose step gradient. The fraction comprising the VLPs was collected from the top of the gradient. The VLPs isolated from the sucrose gradient were analyzed by SDS-PAGE and western immunoblot. These data are on illustrated on FIGS. 1 and 2.

FIG. 1 is a stained SDS-PAGE gel. The lanes in the gel comprise the following: 1 to 5, A/Fujian M1 with 4 different HAs or alone; 6 to 10, A/Indo/M1 with 4 different HAs or alone; 11 to 14, various controls.

Comparing the bands on the gel, the lanes that comprise VLPs comprising avian M1 have stronger bands of M1 and HA in the same lanes, while the lanes that comprise seasonal influenza do not. M1 and HA bands in the same lane is indicative of HA associating with M1. This association is indicative of VLP formation comprising HA and M1. These data provide evidence that avian influenza proteins form VLPs more efficiently than seasonal influenza M1 either with homologous or heterologous envelopes. These data also show that M1 from avian influenza is strongly expressed and stable when compared to seasonal influenza M1.

Figure 2:
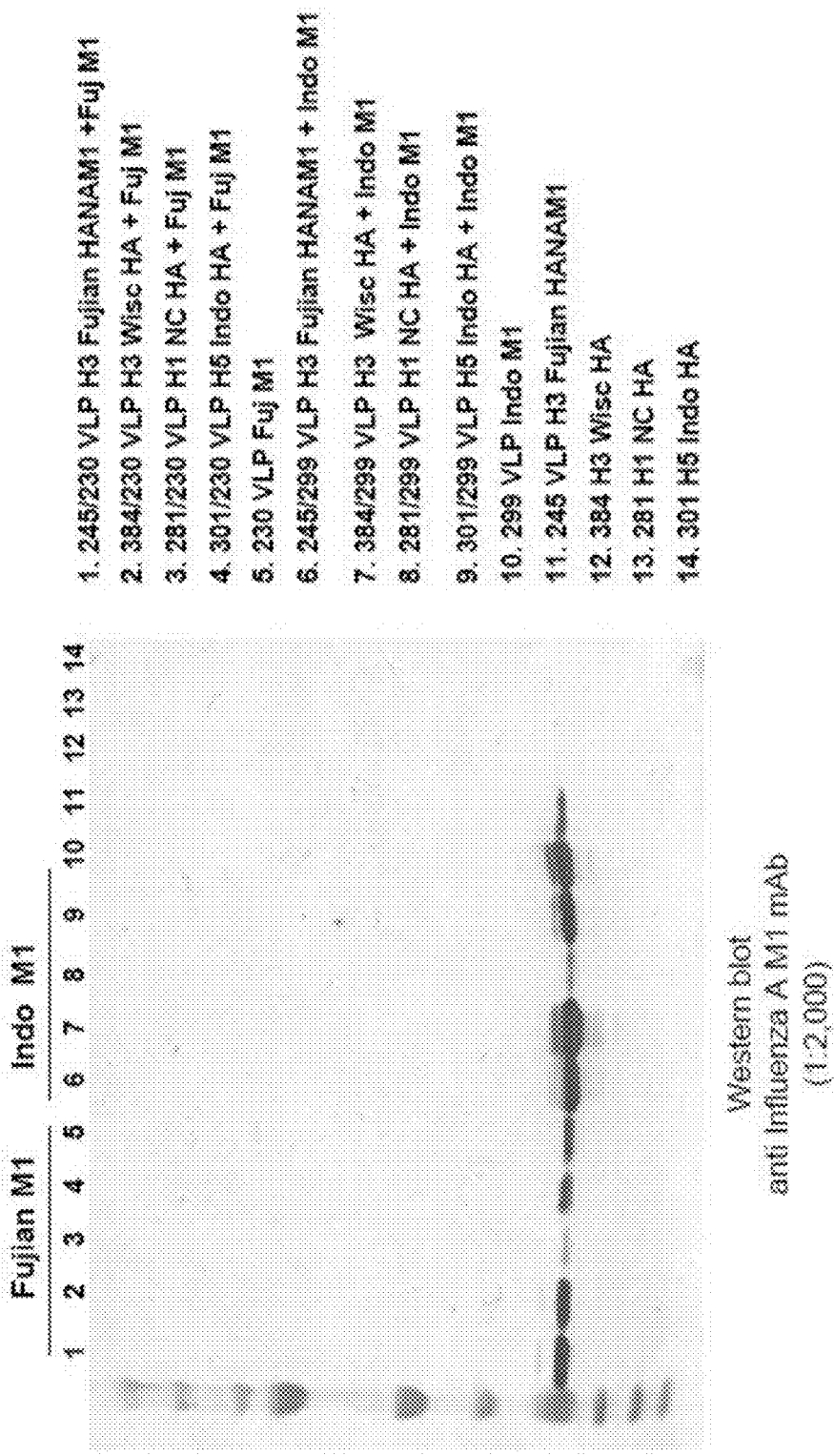
FIG. 2 depicts a stained western blot derived from VLPs made from different constructs after isolation from a sucrose gradient.

FIG. 2 is a western blot showing M1 expression. This blot shows that avian influenza M1 is strongly expressed as compared to seasonal M1. The intensity of the bands indicate that there is more M1, and thus, more VLPs.

Example 2

Expressing Seasonal and Avian VLPs from One Baculovirus Vector

Seasonal and avian influenza M1 and HA proteins were cloned and expressed in a baculovirus expression system. This example, the A/Indonesia/5/05 M1 and A/Fujian/411/2002 HA and NA was cloned into a one baculovirus baculovirus vector. The recombinant virus was infected into Sf9 insect cells and grown under conditions that allow VLP formation. Cells comprising either seasonal HA and M1, avian HA and M1 or a combination of seasonal and avian HA and M1 were grown under conditions that allow formation of VLPs. The seasonal influenza strains used for these experiments were A/Fujian/411/2002 and A/Wisconsin/67/2005 and the avian influenza strain used was A/Indonesia/5/05.

Next, VLPs were harvested and isolated from the supernatant by centrifugation and by a discontinuous sucrose step gradient. The fraction comprising the VLPs was collected from the top of the gradient. The VLPs isolated from the sucrose gradient were analyzed by SDS-PAGE and western immunoblot. These data are on illustrated on FIGS. 3 and 4.

Figure 3:
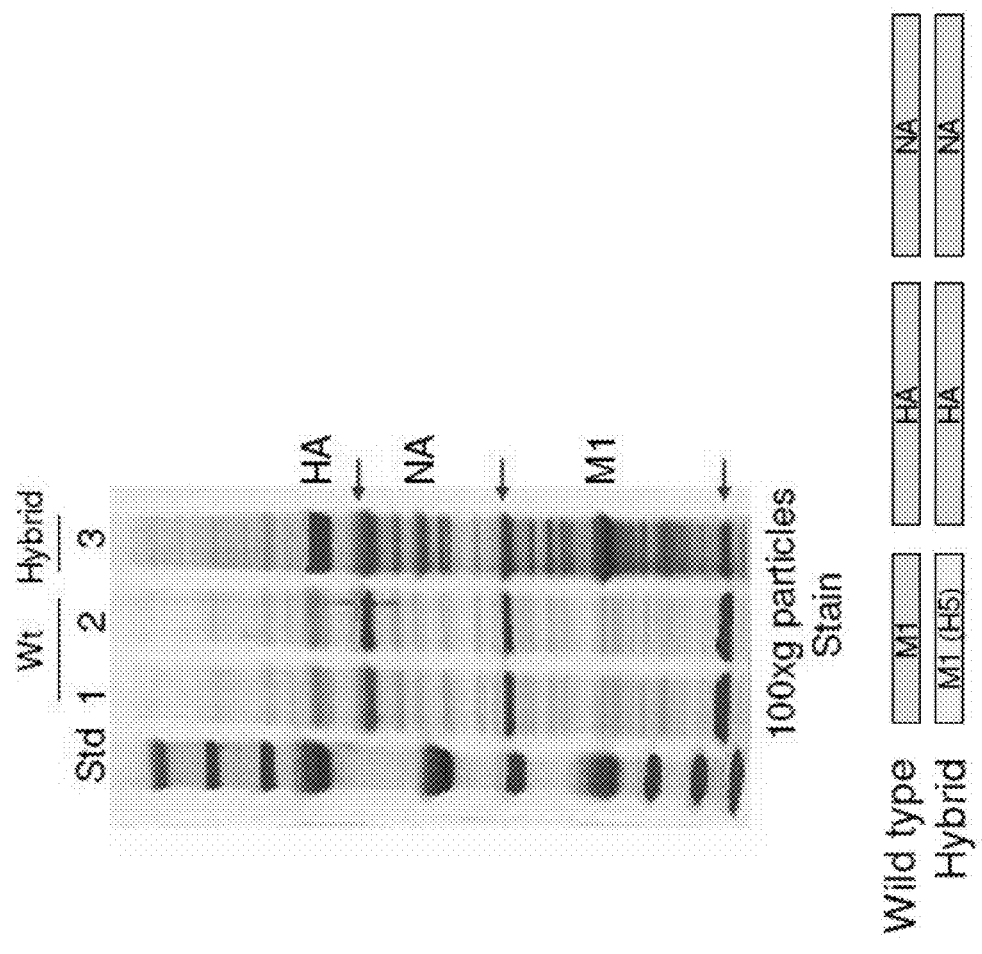
FIG. 3 is a stained SDS-PAGE gel derived from VLPs made from wild type or hybrids of A/Indonesia/5/05 M1 and A/Fujian/411/2002 HA and NA.

FIG. 3 is a stained SDS-PAGE gel. The lanes in the gel comprise the following: 1 and 2 is A/Fujian VLPS (M1, HA and NA) and lane 3 comprises, A/Indo/M1 with A/Fujian HA and NA.

Comparing the bands on the gel, the lane that comprise VLPs from A/Indo/M1 has stronger bands of M1 and HA in the same lanes, while the lanes that comprise A/Fujian do not. M1, HA and NA bands in the same lane is indicative of HA and NA associating with M1. This association is indicative of VLP formation comprising HA, NA and M1. These data provide evidence that avian influenza proteins form VLPs with greater efficiency than seasonal M1 influenza based VLPs. These data also show that M1 from avian influenza is strongly expressed and stable when compared to seasonal influenza M1.

Figure 4:
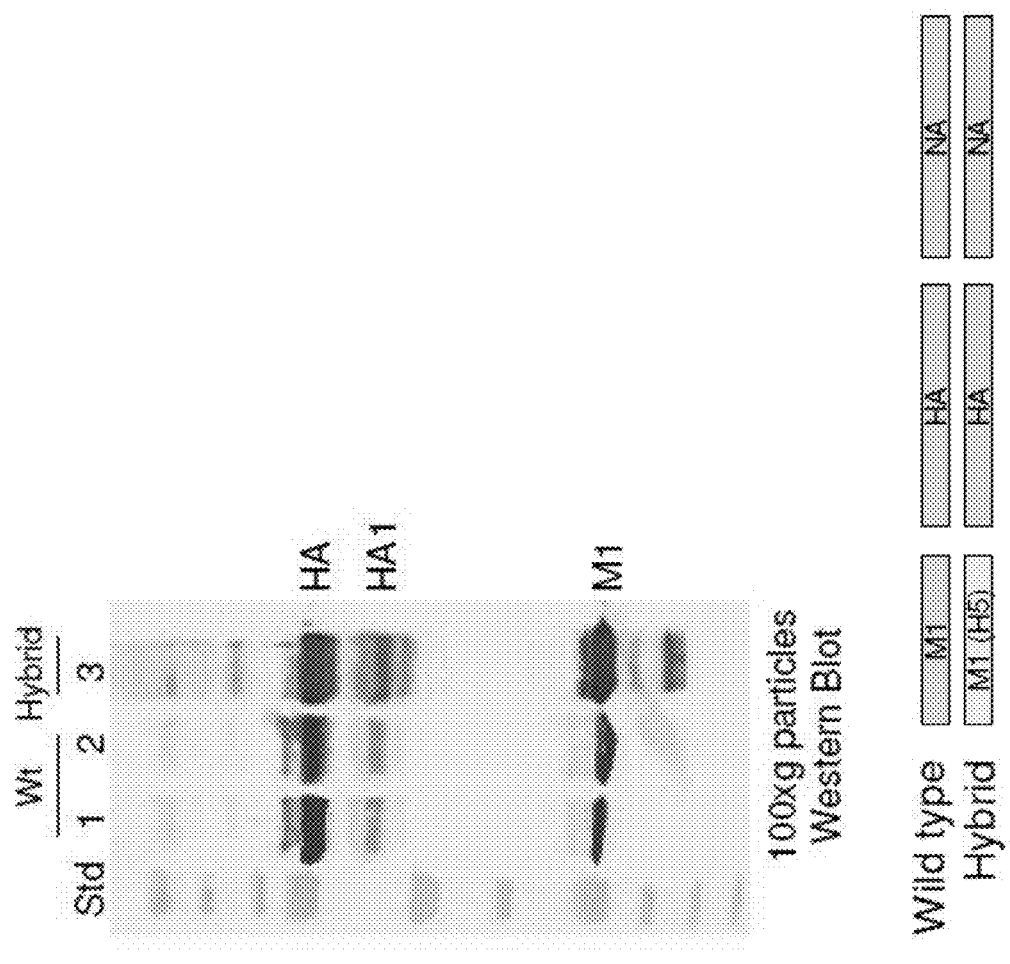
FIG. 4 depicts a stained western blot derived from VLPs made from wild type or hybrids of A/Indonesia/5/05 M1 and A/Fujian/411/2002 HA and NA.

FIG. 4 is a western blot showing M1 expression. This blot shows that VLPs comprising endo A/Indo/M1 and A/Fujian HA, NA are strongly expressed as compared to A/Fujian VLPs. The intensity of the bands indicate that there is more M1, HA and NA in lanes with avian M1 VLPs, and thus, more VLPs.

Example 3

Expressing Chimeric Influenza B HA and NA Constructs Using Common A/Indonesia/5/05 Matrix Protein to Assemble VLPs The sequences below depict the transmembrane and terminal sequences derived from A/Indonesia/5/05 HA and NA (underlined). The transmembrane and terminal sequences of HA and NA molecules can be determined using software prediction by GCG/Accelrys or similar software, as well as by other methods. The exact location of junctions for Indonesia/5/05 sequences can vary.

The sequences below are examples of a chimeric B strain HA with an A/Indonesia/5/05 HA end as well as a chimeric B strain NA with an A/Indo NA substitution of the endodomain and transmembrane regions. These sequences are co-expressed in a baculovirus expression system with an avian influenza M1 protein to produce chimeric VLPs that express influenza B antigens on the surface of VLPs.

free medium (HyClone, Logan, Utah) at 28° C. A Bac-to-Bac baculovirus expression system (Invitrogen, Carlsbad, Calif.) was used with pFastBac 1 transfer vector in *E. coli* DH 10Bac cells for the generation of recombinant baculovirus vectors expressing SARS S and Influenza M1 genes.

SARS coronavirus (SARS-CoV) Urbani strain spike (S) protein amino acids sequence was obtained from NCBI access number AAP13441. The hemagglutinin amino acids sequence of influenza A virus (A/Indonesia/5/05(H5N1)) was obtained from NCBI access number ABP51969. To construct the chimeric SARS S protein, the transmembrane and carboxyl terminal domain (TM/CT) of S protein (aa 1196-1255) was removed, and the TM/CT from Indonesia H5N1 HA (aa 531-568) was added after amino acid 1195 of S protein. The amino acids sequence of the chimeric S-HA protein is shown in FIG. 5 (SEQ ID NO. 10). The matrix protein 1 (M1) amino acids sequence of influenza Indonesia H5N1 was obtained from NCBI access number ABW06359 (FIG. 6).

Figure 7:
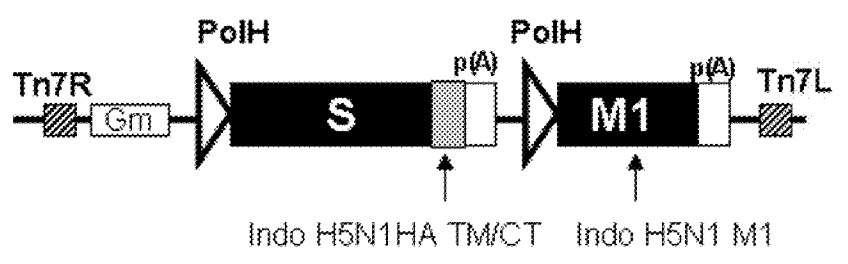

The codon optimized DNA sequences of M1 (SFQ ID NO: 4) and chimeric S for expression in insect cells were synthesized by Geneart (Germany) and subcloned into BamHI and HindIII sites of pFastBac 1 individually. The SnaBI/PvuI fragment containing M1 coding sequence of pFastBac1-M1 was cut and inserted into the HpaI/PvuI fragment containing S coding sequence from pFastBac1-S. The result tandem vector that expresses two proteins is shown in FIG. 7. This vector was used to transform DH10Bac to obtain the bacmid which was transfected into Sf9 cell to obtain the recombinant baculovirus.

```
Hemagglutinin, HA, from Influenza B virus (B/Hong Kong/557/2000)
ABL76892
                                                              (SEQ ID NO. 1)
   1 mkaiivllmv vtsnadrict gitssnsphv vktatqgevn vtgvipltttt ptkshfanlk
  61 gtrtrgklcp dclnctdldv algrpmcvgt tpsakasilh evrpvtsgcf pimhdrtkir
 121 qlpnllrgye nirlstqnvi daekapggpy rlgtsgscpn atsksgffat mawavpkdnn
 181 knatnpltve vpyvcteged qitvwgfhsd nktqmknlyg dsnpqkftss angvtthyvs
 241 qiggfpdqte dgglpqsgri vvdymvqkpg ktgtivyqrg vllpqkvwca sgrskvikgs
 301 lpligeadcl hekygglnks kpyytgehak aigncpiwvk tplklangtk yrppakllke
 361 rgffgaiagf leggwegmia gwhgytshga hgvavaadlk stqeainkit knlnslsele
 421 vknlqrlsga mdelhneile ldekvddlra dtissqiela vllsnegiin sedehllale
 481 rklkkmlgps avdigngcfe tkhkcnqtcl driaagtfna gefslptfds lnitaaslnd
 541 dgldnhtQIL SIYSTVASSL ALAIMMAGLS LWMCSNGSLQ CRICI Neuraminidase, NA, from Flu B/Shanghai/361/02
ISDN129538
                                                              (SEQ ID NO. 2)
MNPNQKIITIGSICMVIGIVSLMLQIGNMISSDILLKFSTTEITAPTMPLDCANASNVQAVNRSATKG
VTLLLPEPEWTYPRLSCPGSTFQKALLISPHRFGETKGNSAPLIIREPFIACGPKECKHFALTHYAAQ
PGGYYNGTREDRNKLRHLISVKLGKIPTVENSIFHMAAWSGSACHDGKEWTYIGVDGPDSNALLKIKY
GEAYTDTYHSYANNILRTQESACNCIGGNCYLMITDGSASGISECRFLKIREGRIIKEIFPTGRVKHT
EECTCGFASNKTIECACRDNSYTAKRPFVKLNVETDTAEIRLMCTETYLDTPRPDDGSITGPCESNGN
KGSGGIKGGFVHQRMASKIGRWYSRTMSKTKRMGMGLYVKYDGDPWIDSDALALSGVMVSMEEPGWYS
FGFEIKDKKCDVPCIGIEMVHDGGKETWHSAATAIYCLMGSGQLLWDTVTGVDMAL M1 from A/Indonesia
                                                              (SEQ ID NO. 3)
MSLLTEVETY VLSIIPSGPL KAEIAQKLED VFAGKNTDLE ALMEWLKTRP ILSPLTKGIL
GFVFTLTVPS ERGLQRRRFV QNALNGNGDP NNMDRAVKLY KKLKREITFH GAKEVSLSYS
TGALASCMGL IYNRMGTVTT EVAFGLVCAT CEQIADSQHR SHRQMATITN PLIRHENRMV
LASTTAKAME QMAGSSEQAA EAMEVANQAR QMVQAMRTIG THPNSSAGLR DNLLENLQAY
QKRMGVQMQR FK
```

Example 4

Making Chimeric VLPs with Coronavirus S Protein

Materials and Methods

*Spodoptera frugiperda* Sf9 insect cells (ATCC CRL-1711) were maintained as suspension in HyQ-SFX insect serum VLPs Expression, Purification and Characterizations Sf9 insect cells were infected for 64 hours at a cell density of $2 \times 10^6$ cells/ml with recombinant baculoviruses that express both chimeric SARS S and Indo M1 at a MOI=1. Culture supernatants were harvest by centrifuge at 4000 g. The cell free supernatants were concentrated by ultrafiltration (UF) with a 500 kDa MWCO hollow fiber filter (GE healthcare). The retentate was buffer exchanged with diafiltration (DF) to 25 mM TrisCl pH 8.0, 300 mM NaCl. The UF/DF retentate was loaded on an ion exchange column (Fractogel TMAE, EMD) equilibrium in the same buffer. VLPs passed through from the column while baculovirus and DNA bound to the column. The flow through fractions containing VLPs were further concentrated with ultrafiltration before load to a Sephacryl S500 size exclusion column (GE healthcare).

The pool of VLPs peak from size exclusion column was analyzed with SDS-PAGE (4-12% Bis-Tris NuPage, Invitrogen) and densitometry for purity. The VLPs were also analyzed with particle size analyzer (Malvern Zetasizer NanoSeries NanoZS) and electron microscopy. The antibodies used in this study were from the following vendors: rabbit anti-SARS S and normal anti-rabbit IgG (IMGNEX), rabbit anti-SARS M (Abgent), mouse anti-influenza M1 (Serotec).

Results

Figure 8:
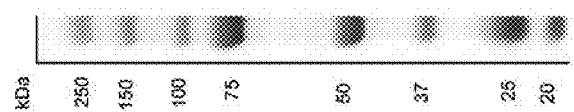
FIG. 8 depicts the purified SARS S/Indo M1 chimeric VLPs. Lane 1 is Coomassie blue stain. Lane 2 is western blot, top panel: anti SARS S; bottom panel: anti influenza M1.

Purified SARS S/Indo M1 chimeric VLPs were analyzed by SDS-PAGE, densitometry and western blot (FIG. 8). The purity for SARS S protein was 13.7% and purity for Indo M1 protein was 67.6%. The combined purity for the S and M 1 is 81.3%. The western blot confirmed the identity of S and M1 (FIG. 8, lane 2).

Figure 9:
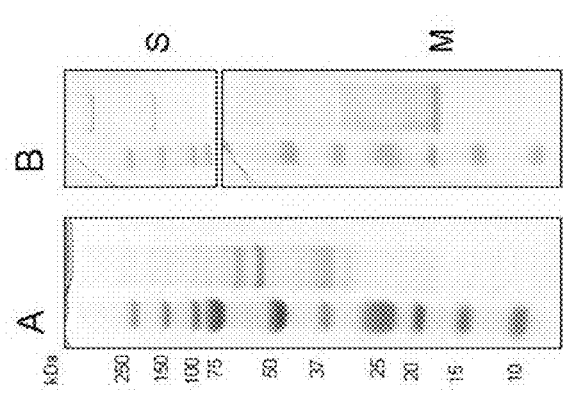
FIG. 9 depicts purified wild type SARS VLPs composed of SARS S, M and E proteins. A) Coomassie blue stain; B) Western blot, top panel: anti SARS S; bottom panel: anti SARS M.

Recombinant baculovirus that expressed SARS spike (S), membrane (M) and envelope (E) proteins in a tandem manner were also expressed. We expressed and purified the wild type SARS VLPs with the same protocol that was used to purify chimeric VLPs. The purity of wild type SARS VLPs (no influenza proteins) were analyzed by SDS-PAGE and western blot (FIG. 9). The S and M proteins can hardly be seen in the coomassie stained gel and the contaminant proteins were much more prominent. The data indicate that wild type SARS VLPs are insufficient to form in the baculovirus insect cell expression system while the SARS S/Indo M1 chimeric VLPs an greatly improve the yield and purity of the product VLPs.

Figure 10:
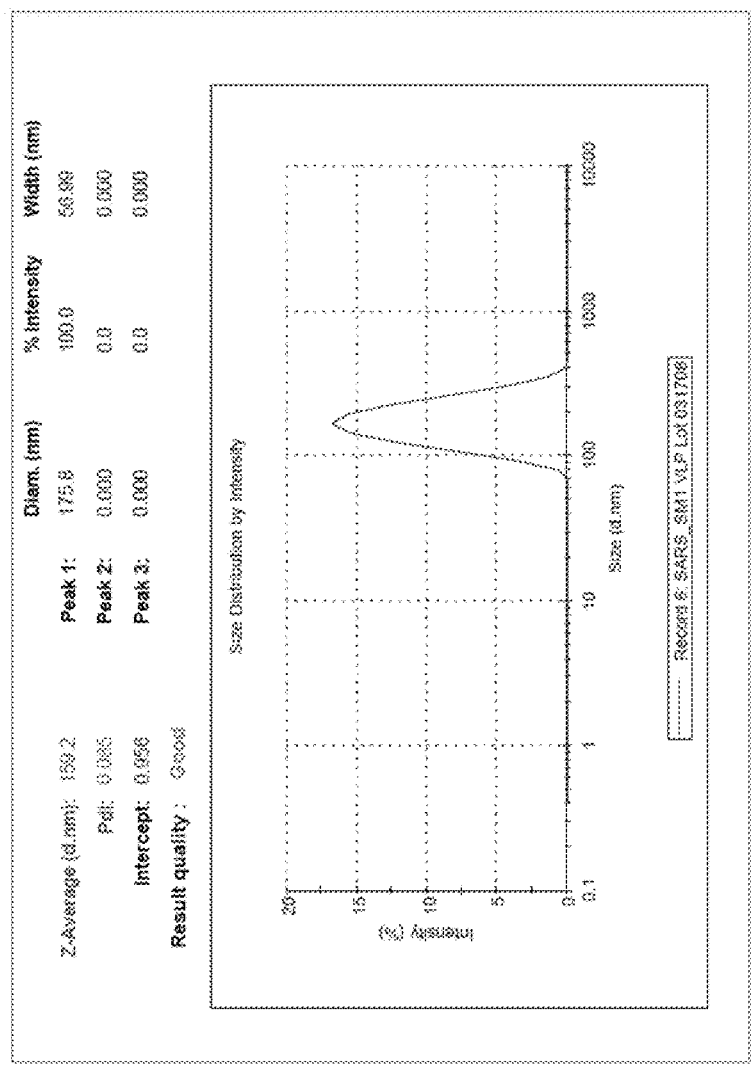
FIG. 10 depicts particle size analysis result for SARS S/Indo M1 chimeric VLPs with Malvern Zetasizer.
Figure 11:
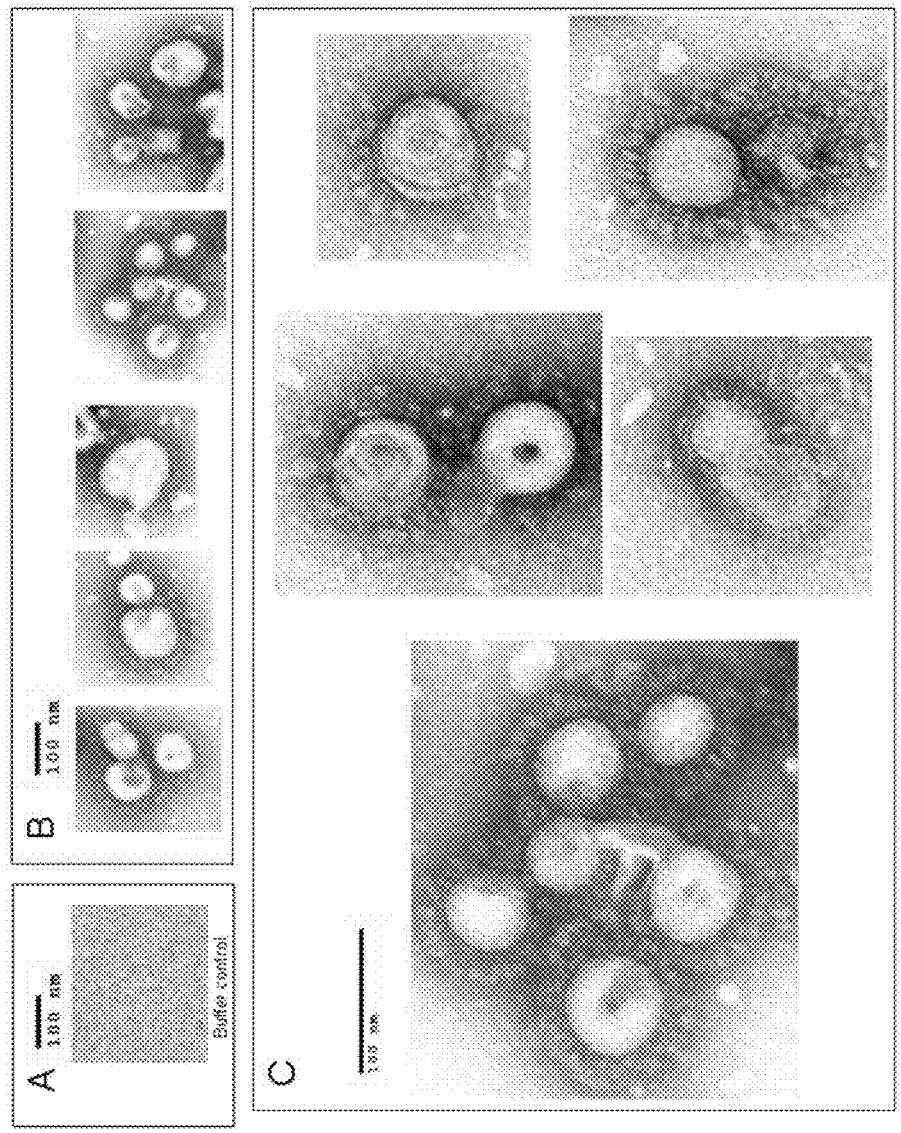
FIG. 11A-C depicts electron microscope (EM) negative stain of SARS S/Indo M1 chimeric VLPs. A) EM image for buffer control; B) Selected EM images for VLPs; C) Selected EM images for VLPs at higher magnitude.
Figure 12:
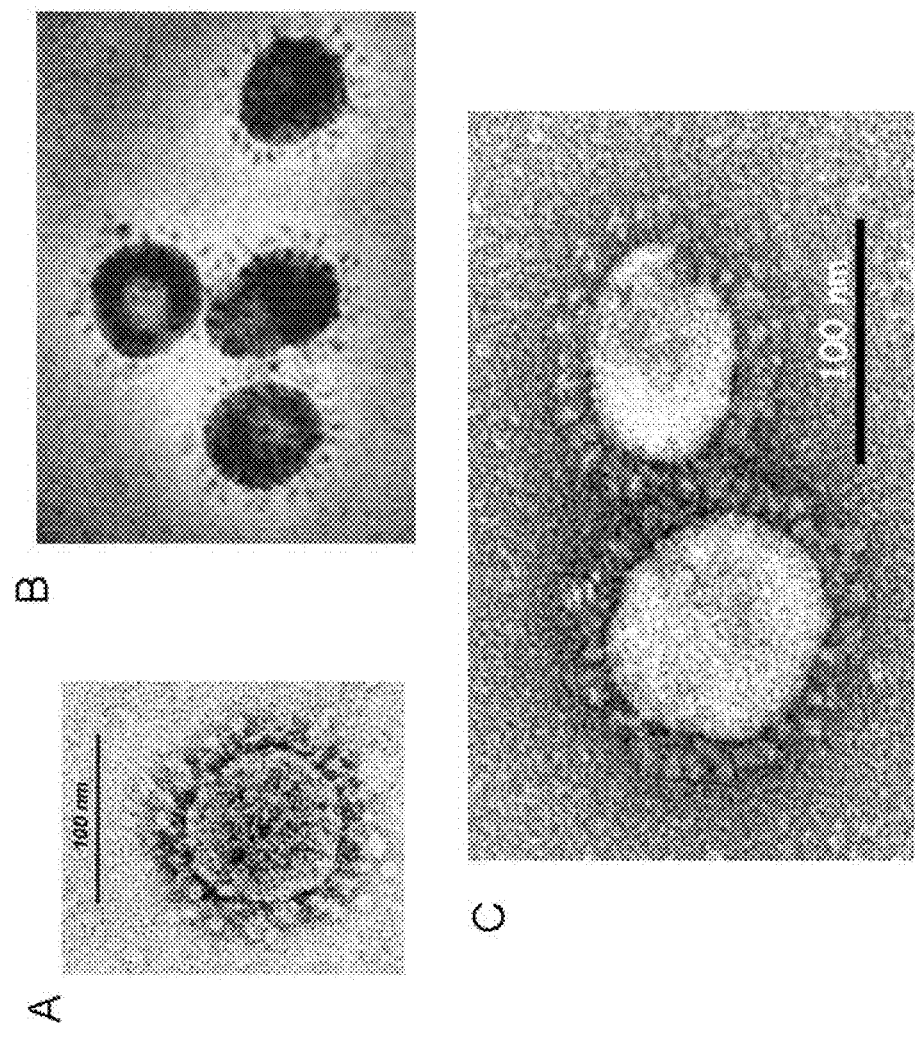
FIG. 12A-C depicts Published EM images for SARS-CoV and coronavirus.

Next, we analyzed the average particle size of purified chimeric VLPs to be 159.2 nm (FIG. 10). The chimeric VLPs were imaged with electron microscopy (EM) negative stain (FIG. 11). The size and morphology of chimeric VLPs are very similar to the published EM images of SARS coronavirus (FIG. 12). They are about 100 nm diameter with corona structure on the outer rim. The immuno-gold EM with anti-SARS S antibody confirmed that SARS S proteins were located on the surface of chimeric VLPs (FIG. 12).

The inventors have engineered a chimeric VLP comprising the major spike (S) gene of coronavirus (CoV) that causes SARS. A CoV S chimeric envelope glycoprotein was made by replacing the transmembrane and C-terminus (endodomain) with analogous sequences from the avian influenza HA (A/Indonesia/5/05H5N1 strain). Unexpected high levels of SARS VLPs were produced in Sf9 insect cells infected with a baculovirus expressing the chimeric SARS S glycoprotein and the avian M1 matrix protein. Chimeric VLPs comprising S protein have the morphology that is nearly identical to the wild type CoV with the recombinant, chimeric S spike protein forming a corona (crown)—envelope in a lipid envelope on spherical particles with an avian influenza M1 core. These recombinant chimeric SARS-avain flu VLPs are efficiently produced in insect cells and were purified as described above.

These data provide an excellent example that avian M1, e.g. Indonesia H5N1 M1 protein, can form chimeric VLPs with surface antigen from other virus such as SARS-CoV. The chimeric VLPs with avian influenza protein as backbone can be purified through a manufacturing friendly procedure that requires only two steps of chromatography. The size and morphology of the chimeric VLPs are similar to the wild type viruses that carry the same surface antigen.

Example 5

Chimeric Influenza B VLPs

Influenza B virus antigen is an important component of seasonal influenza vaccines. The expression levels of influenza B antigen are critically important for ensuring timely delivery of sufficient number of influenza vaccine doses, otherwise vaccine shortages can occur. Influenza B VLPs for B/Florida/4/06 consist of three proteins, HA (SEQ ID NO 8), NA (SEQ ID NO. 9), and M1 (matrix), which are assembled into VLP structure. HA and NA genes where obtained by RT-PCR from the influenza B/Florida/4/06 virus. In order to improve expression levels of influenza B VLPs, VLPs using three different M1 proteins were made. One M1 protein is derived from the B/Florida/4/06 virus. The second M1 gene is derived from influenza B/Ann Arbor/1/1986 strain, which is often used for preparation of live reassortant influenza B viruses in current influenza vaccine industry. The third M1 is derived from avian influenza A/Indonesia/5/05 (H5N1) virus. Thus, three types of influenza B/Florida/4/06 VLPs have been produced in Sf9 cells, and expression levels have been compared.

Methods.

Baculoviruses were engineered to express full length HA, NA, and M1 genes of influenza. HA (SEQ ID NO: 5) and NA (SEQ ID NO: 6) genes were obtained by RT-PCR from the influenza B/Florida/4/06 virus. M1 gene has been also generated by RT-PCR from the influenza B/Florida/4/06 virus. Alternatively, M1 gene of B/Ann Arbor/1/1986 was synthesized (GeneArt, Germany) and M1 gene of influenza A/Indonesia/5/05 (H5N1) was also synthesized (GeneArt, Germany). Each gene was cloned into a pFastBac1 vector under the control of the baculovirus polyhedrin promoter (Invitrogen). Then, HA, NA, and M1 genes were combined into tandem vectors as shown on FIG. 13. Then, tandem gene constructs were transferred to an AcMNPV baculovirus Bacmid vectors (Invitrogen), the Bacmid DNAs were purified and used to transfect Sf9 insect cells. The resulting recombinant baculoviruses were plaque-purified and virus stocks prepared in Sf9 cells.

Figure 14:
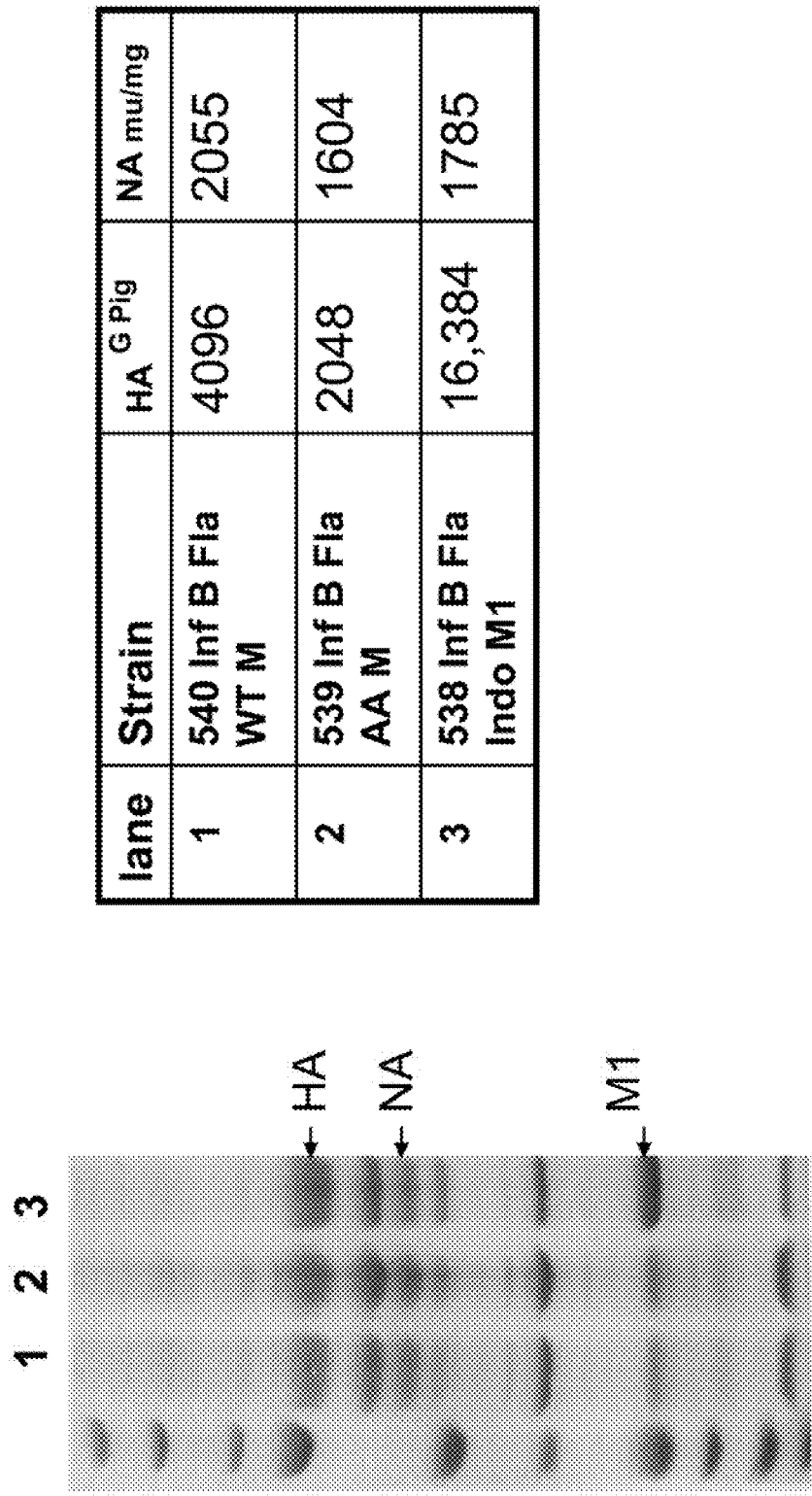
FIG. 14 depicts expression levels of influenza B/Florida/4/06 VLPs by Coomassie staining (left panel) and HA/NA assays (right panel). Lane 1. Sample of B/Florida/4/06 VLPs containing B/Florida/4/06 M1, Lane 2. Sample of B/Florida/4/06 VLPs containing B/Ann Arbor/1/1986 M1, Lane 3 Sample of B/Florida/4/06 VLPs containing A/Indonesia/5/05 (H5N1) M1. The right panels shows HA and NA activity by the hemagglutination and neuraminidase enzyme activity essays.

About 30 ml of SP) cells, at about $2 \times 10^6$ cells/ml in a 125 mL shaker flasks, were infected with recombinant baculoviruses expressing HA, NA, and M1 genes at a multiplicity of infection (MOI) of 1-3 infectious particles per ml (pfu), incubated at 27° C. with constant shaking, then harvested at 66-72 hours post infection. The media was removed by low speed centrifugation. Then, media were clarified using filtration through 0.45 µM filters and the media were subjected to ultracentrifugation for 1 hour at 26,000 rpm through 30% sucrose layer. Pellets were resuspended in 200 mL of PBS and analyzed by SDS-PAGE and western blot (FIG. 14). Resuspended pellets were also analyzed for ability to agglutinate guinea pig red blood cells in Win). The data are shown on FIG. 14. The resuspended pellets have been also analyzed by negative staining transmission electron microscopy.

Results.

M1 derived from influenza A/Indonesia/5/05 (H5N1) showed significantly higher expression levels by Coomassie gel staining (FIG. 14, lane 3) compared to VLPs made using B/Florida/4/06 M1 or B/Ann Arbor/1/1986 M1. Also, HA titers of VLPs containing influenza A/Indonesia/5/05 (H5N1) M1, were 4-8 times higher as compared to the other two VLP types. Electron microscopy of VLPs containing influenza A/Indonesia/5/05 (H5N1) M1 had higher concentration of VLP and more regular spherical shape as compared to the other two VLPs (FIG. 15).

Example 6

Making Chimeric VLPs with RSV F1 Protein

*Spodoptera frugiperda* Sf9 insect cells are maintained and grown as essentially described above. The codon optimized DNA sequences of influenza M1 (SEQ ID NO: 3) and chimeric RSV F1 (HA TM/CY (SEQ ID NO: 11)) for expression in insect cells are synthesized and subcloned into pFastBac 1. The result vector expresses both proteins. This vector is used to transform DH10Bac to obtain the bacmid which is transfected into Sf9 cell to obtain the recombinant baculovirus.

Sf9 insect cells are infected for 64 hours at a cell density of $2 \times 10^6$ cells/ml with recombinant baculoviruses that express both chimeric RSV F1 (SEQ ID NO: 12) and Indo M1 (SEQ ID NO: 3) at a MOI=1. Culture supernatants are harvest by centrifuge at 4000 g. The cell free supernatants are concentrated by ultrafiltration (UF) with a 500 kDa MWCO hollow fiber filter (GE healthcare). The retentate is buffer exchanged with diafiltration (DF) to 25 mM TrisCl pH 8.0, 300 mM NaCl. The UF/DF retentate is loaded on an ion exchange column (Fractogel TMAE, EMD). VLPs pass through from the column while baculovirus and DNA binds to the column. The flow through fractions containing VLPs are further concentrated with ultrafiltration before loading onto a Sephacryl 5500 size exclusion column (GE healthcare).

The pool of VLPs peak from size exclusion column is analyzed with SDS-PAGE (4-12% Bis-Tris NuPage, Invitrogen) and densitometry for purity. The VLPs are also analyzed with particle size analyzer (Malvern Zetasizer NanoSeries NanoZS), SDS PAGE, western blot analysis, and electron microscopy.

All patents, publications and patent applications herein are incorporated by reference to the same extent as if each individual patent, publication or cited patent application was specifically and individually indicated to be incorporated by reference.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method of increasing the efficiency of influenza virus-like particle (VLP) production comprising expressing an avian influenza matrix (M1) protein and at least one non-avian influenza protein in a host cell,
   wherein the avian influenza M1 protein is derived from A/Indonesia/5/05 influenza, and
   whereby increased VLP production is obtained in the host cell comprising the avian influenza M1 protein compared to a host cell expressing a non-avian influenza M1 protein.

2. The method of claim 1, wherein said A/Indonesia/5/05 M1 protein comprises the amino acid sequence of SEQ ID NO: 3.

3. The method of claim 1, wherein said non-avian influenza protein is an influenza hemagglutinin (HA) protein.

4. The method of claim 3, wherein said influenza HA protein is derived from a strain of seasonal influenza virus.

5. The method of claim 3, wherein said influenza HA protein has hemagglutinin activity.

6. The method of claim 3, wherein said influenza HA protein is a chimeric protein.

7. The method of claim 6, wherein said chimeric protein comprises the external domain of non-avian influenza HA protein fused to the transmembrane and/or cytoplasmic terminal domains of an avian influenza HA protein.

8. The method of claim 7, wherein said avian influenza HA protein is derived from influenza strain A/Indonesia/5/05.

9. The method of claim 1, wherein said non-avian influenza protein is an influenza neuraminidase (NA) protein.

10. The method of claim 9, wherein said influenza NA protein is derived from a strain of seasonal influenza virus.

11. The method of claim 9, wherein said influenza NA protein has neuraminidase activity.

12. The method of claim 9, wherein said influenza NA protein is a chimeric protein.

13. The method of claim 12, wherein said chimeric protein comprises the external domain of non-avian influenza NA protein fused to the transmembrane and/or cytoplasmic terminal domains of an avian influenza NA protein.

14. The method of claim 13, wherein said avian influenza NA protein is derived from influenza strain A/Indonesia/5/05.

15. The method of claim 1, wherein said host cell is selected from the group consisting of yeast, insect, amphibian, avian, and mammalian cells.

* * * * *

SEQUENCE LISTING

```
<160> NUMBER OF SEQ ID NOS: 12

<210> SEQ ID NO 1
<211> LENGTH: 585
<212> TYPE: PRT
<213> ORGANISM: Influenza B virus

<400> SEQUENCE: 1

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140
```

-continued

```
Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
            165                 170                 175

Lys Asp Asn Asn Lys Asn Ala Thr Asn Pro Leu Thr Val Glu Val Pro
        180                 185                 190

Tyr Val Cys Thr Glu Gly Glu Asp Gln Ile Thr Val Trp Gly Phe His
    195                 200                 205

Ser Asp Asn Lys Thr Gln Met Lys Asn Leu Tyr Gly Asp Ser Asn Pro
210                 215                 220

Gln Lys Phe Thr Ser Ser Ala Asn Gly Val Thr Thr His Tyr Val Ser
225                 230                 235                 240

Gln Ile Gly Gly Phe Pro Asp Gln Thr Glu Asp Gly Gly Leu Pro Gln
                245                 250                 255

Ser Gly Arg Ile Val Val Asp Tyr Met Val Gln Lys Pro Gly Lys Thr
                260                 265                 270

Gly Thr Ile Val Tyr Gln Arg Gly Val Leu Leu Pro Gln Lys Val Trp
            275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
            355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Gln Ile Glu Leu Ala Val Leu Leu Ser
450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
530                 535                 540

Asn His Thr Gln Ile Leu Ser Ile Tyr Ser Thr Val Ala Ser Ser Leu
545                 550                 555                 560

Ala Leu Ala Ile Met Met Ala Gly Leu Ser Leu Trp Met Cys Ser Asn
                565                 570                 575
```

```
Gly Ser Leu Gln Cys Arg Ile Cys Ile
        580                 585

<210> SEQ ID NO 2
<211> LENGTH: 464
<212> TYPE: PRT
<213> ORGANISM: Influenza B Virus

<400> SEQUENCE: 2

Met Asn Pro Asn Gln Lys Ile Ile Thr Ile Gly Ser Ile Cys Met Val
1               5                   10                  15

Ile Gly Ile Val Ser Leu Met Leu Gln Ile Gly Asn Met Ile Ser Ser
            20                  25                  30

Asp Ile Leu Leu Lys Phe Ser Thr Thr Glu Ile Thr Ala Pro Thr Met
        35                  40                  45

Pro Leu Asp Cys Ala Asn Ala Ser Asn Val Gln Ala Val Asn Arg Ser
50                  55                  60

Ala Thr Lys Gly Val Thr Leu Leu Leu Pro Glu Pro Glu Trp Thr Tyr
65                  70                  75                  80

Pro Arg Leu Ser Cys Pro Gly Ser Thr Phe Gln Lys Ala Leu Leu Ile
                85                  90                  95

Ser Pro His Arg Phe Gly Glu Thr Lys Gly Asn Ser Ala Pro Leu Ile
            100                 105                 110

Ile Arg Glu Pro Phe Ile Ala Cys Gly Pro Lys Glu Cys Lys His Phe
        115                 120                 125

Ala Leu Thr His Tyr Ala Ala Gln Pro Gly Gly Tyr Tyr Asn Gly Thr
130                 135                 140

Arg Glu Asp Arg Asn Lys Leu Arg His Leu Ile Ser Val Lys Leu Gly
145                 150                 155                 160

Lys Ile Pro Thr Val Glu Asn Ser Ile Phe His Met Ala Ala Trp Ser
                165                 170                 175

Gly Ser Ala Cys His Asp Gly Lys Glu Trp Thr Tyr Ile Gly Val Asp
            180                 185                 190

Gly Pro Asp Ser Asn Ala Leu Leu Lys Ile Lys Tyr Gly Glu Ala Tyr
        195                 200                 205

Thr Asp Thr Tyr His Ser Tyr Ala Asn Asn Ile Leu Arg Thr Gln Glu
210                 215                 220

Ser Ala Cys Asn Cys Ile Gly Gly Asn Cys Tyr Leu Met Ile Thr Asp
225                 230                 235                 240

Gly Ser Ala Ser Gly Ile Ser Glu Cys Arg Phe Leu Lys Ile Arg Glu
                245                 250                 255

Gly Arg Ile Ile Lys Glu Ile Phe Pro Thr Gly Arg Val Lys His Thr
            260                 265                 270

Glu Glu Cys Thr Cys Gly Phe Ala Ser Asn Lys Thr Ile Glu Cys Ala
        275                 280                 285

Cys Arg Asp Asn Ser Tyr Thr Ala Lys Arg Pro Phe Val Lys Leu Asn
290                 295                 300

Val Glu Thr Asp Thr Ala Glu Ile Arg Leu Met Cys Thr Glu Thr Tyr
305                 310                 315                 320

Leu Asp Thr Pro Arg Pro Asp Asp Gly Ser Ile Thr Gly Pro Cys Glu
                325                 330                 335

Ser Asn Gly Asn Lys Gly Ser Gly Gly Ile Lys Gly Gly Phe Val His
            340                 345                 350

Gln Arg Met Ala Ser Lys Ile Gly Arg Trp Tyr Ser Arg Thr Met Ser
        355                 360                 365
```

```
Lys Thr Lys Arg Met Gly Met Gly Leu Tyr Val Lys Tyr Asp Gly Asp
    370                 375                 380
Pro Trp Ile Asp Ser Asp Ala Leu Ala Leu Ser Gly Val Met Val Ser
385                 390                 395                 400
Met Glu Glu Pro Gly Trp Tyr Ser Phe Gly Phe Glu Ile Lys Asp Lys
                405                 410                 415
Lys Cys Asp Val Pro Cys Ile Gly Ile Glu Met Val His Asp Gly Gly
                420                 425                 430
Lys Glu Thr Trp His Ser Ala Ala Thr Ala Ile Tyr Cys Leu Met Gly
            435                 440                 445
Ser Gly Gln Leu Leu Trp Asp Thr Val Thr Gly Val Asp Met Ala Leu
450                 455                 460

<210> SEQ ID NO 3
<211> LENGTH: 252
<212> TYPE: PRT
<213> ORGANISM: Influenza A Virus

<400> SEQUENCE: 3

Met Ser Leu Leu Thr Glu Val Glu Thr Tyr Val Leu Ser Ile Ile Pro
1               5                   10                  15
Ser Gly Pro Leu Lys Ala Glu Ile Ala Gln Lys Leu Glu Asp Val Phe
            20                  25                  30
Ala Gly Lys Asn Thr Asp Leu Glu Ala Leu Met Glu Trp Leu Lys Thr
        35                  40                  45
Arg Pro Ile Leu Ser Pro Leu Thr Lys Gly Ile Leu Gly Phe Val Phe
50                  55                  60
Thr Leu Thr Val Pro Ser Glu Arg Gly Leu Gln Arg Arg Arg Phe Val
65                  70                  75                  80
Gln Asn Ala Leu Asn Gly Asn Gly Asp Pro Asn Asn Met Asp Arg Ala
                85                  90                  95
Val Lys Leu Tyr Lys Lys Leu Lys Arg Glu Ile Thr Phe His Gly Ala
            100                 105                 110
Lys Glu Val Ser Leu Ser Tyr Ser Thr Gly Ala Leu Ala Ser Cys Met
        115                 120                 125
Gly Leu Ile Tyr Asn Arg Met Gly Thr Val Thr Thr Glu Val Ala Phe
130                 135                 140
Gly Leu Val Cys Ala Thr Cys Glu Gln Ile Ala Asp Ser Gln His Arg
145                 150                 155                 160
Ser His Arg Gln Met Ala Thr Ile Thr Asn Pro Leu Ile Arg His Glu
                165                 170                 175
Asn Arg Met Val Leu Ala Ser Thr Thr Ala Lys Ala Met Glu Gln Met
            180                 185                 190
Ala Gly Ser Ser Glu Gln Ala Ala Glu Ala Met Glu Val Ala Asn Gln
        195                 200                 205
Ala Arg Gln Met Val Gln Ala Met Arg Thr Ile Gly Thr His Pro Asn
210                 215                 220
Ser Ser Ala Gly Leu Arg Asp Asn Leu Leu Glu Asn Leu Gln Ala Tyr
225                 230                 235                 240
Gln Lys Arg Met Gly Val Gln Met Gln Arg Phe Lys
                245                 250

<210> SEQ ID NO 4
<211> LENGTH: 759
<212> TYPE: DNA
<213> ORGANISM: Influenza A Virus
```

-continued

<400> SEQUENCE: 4

```
atgtccctgc tgaccgaggt ggagacctac gtgctgtcca tcatcccctc cggtcctctg     60
aaggctgaga tcgctcagaa gctcgaggac gttttcgctg gcaagaacac cgacctcgag    120
gctctgatgg agtggctcaa gacccgtccc atcctgtccc ccctgaccaa gggtatcctg    180
ggtttcgtgt tcaccctgac cgtgccctcc gagcgtggtc tgcagcgtcg tcgtttcgtg    240
cagaacgctc tgaacggtaa cggtgacccc aacaacatgg accgtgctgt gaagctgtac    300
aagaagctga agcgcgagat caccttccac ggtgctaagg aggtgtccct gtcctactcc    360
accggtgctc tggctagctg catgggcctg atctacaacc gtatgggcac cgtgaccacc    420
gaggtggcct tcggtctggt ctgcgctacc tgcgagcaga tcgctgactc ccagcaccgt    480
tcccaccgtc agatggctac catcaccaac cccctgatcc gtcacgagaa ccgtatggtg    540
ctggcttcca ccaccgctaa ggctatggag cagatggctg gttcctccga gcaggctgct    600
gaggccatgg aggtggccaa ccaggctcgt cagatggtgc aggctatgcg taccatcggc    660
acccacccca actcctccgc tggtctgcgt gacaacctgc tcgagaacct gcaggcttac    720
cagaagcgta tgggagtcca gatgcagcgc ttcaagtaa                           759
```

<210> SEQ ID NO 5
<211> LENGTH: 1755
<212> TYPE: DNA
<213> ORGANISM: Influenza B Virus

<400> SEQUENCE: 5

```
atgaaggcaa taattgtact actcatggta gtaacatcca atgcagatcg aatctgcact     60
ggaataacat cttcaaactc acctcatgtg gtcaaaacag ccactcaagg ggaggtcaat    120
gtgactggtg tgataccact aacaacaaca ccaacaaaat cttattttgc aaatctcaaa    180
ggaacaagga ccagagggaa actatgccca gactgtctca actgcacaga tctggatgtg    240
gctttgggca gaccaatgtg tgtggggacc acaccttcgg cgaaagcttc aatactccac    300
gaagtcaaac ctgttacatc cgggtgcttt cctataatgc acgacagaac aaaaatcagg    360
caactaccca atcttctcag aggatatgaa aatatcaggc tatcaaccca aaacgtcatc    420
gatgcggaaa aggcaccagg aggaccctac agacttggaa cctcaggatc ttgccctaac    480
gctaccagta agagcggatt tttcgcaaca atggcttggg ctgtcccaaa ggacaacaac    540
aaaaatgcaa cgaacccact aacagtagaa gtaccataca tttgtacaga aggggaagac    600
caaatcactg tttgggggtt ccattcagat aacaaaaccc aaatgaagaa cctctatgga    660
gactcaaatc ctcaaaagtt cacctcatct gctaatggag taaccacaca ctatgtttct    720
cagattggca gcttcccaga tcaaacagaa gacggaggac taccacaaag cggcaggatt    780
gttgttgatt acatgatgca aaaacctggg aaaacaggaa caattgtcta ccaaagaggt    840
gttttgttgc ctcaaaaggt gtggtgcgcg agtggcagga gcaaagtaat aaaagggtcc    900
ttgcctttaa ttggtgaagc agattgcctt catgaaaaat acggtggatt aaacaaaagc    960
aagccttact acacaggaga acatgcaaaa gccataggaa attgcccaat atgggtgaaa   1020
acacctttga agcttgccaa tggaaccaaa tatagacctc ctgcaaaact attaaaggaa   1080
aggggtttct tcggagctat tgctggtttc ctagaaggag gatgggaagg aatgattgca   1140
ggctggcacg gatacacatc tcacggagca catggagtgg cagtggcggc ggaccttaag   1200
agtacgcaag aagctataaa caagataaca aaaaatctca attctttgag tgagctagaa   1260
gtaaagaatc ttcaaagact aagtggtgcc atggatgaac tccacaacga aatactcgag   1320
```

```
ctggatgaga aagtggatga tctcagagct gacactataa gctcgcaaat agaacttgca    1380
gtcttgcttt ccaacgaagg aataataaac agtgaagatg agcatctatt ggcacttgag    1440
agaaaactaa agaaaatgct gggtccctct gctgtagaga taggaaatgg atgcttcgaa    1500
accaaacaca agtgcaacca gacctgctta gacaggatag ctgctggcac ctttaatgca    1560
ggagagtttt ctctccccac ttttgattca ctgaacatta ctgctgcatc tttaaatgat    1620
gatggattgg ataaccatac tatactgctc tattactcaa ctgctgcttc tagtttggct    1680
gtaacattga tgctagctat ttttattgtt tatatggtct ccagagacaa cgtttcatgc    1740
tccatctgtc tataa                                                    1755

<210> SEQ ID NO 6
<211> LENGTH: 1401
<212> TYPE: DNA
<213> ORGANISM: Influenza B Virus

<400> SEQUENCE: 6
atgctacctt caactataca aacgttaacc ctatttctca catcaggggg agtgttatta     60
tcactatatg tgtcagcttc attgtcatac ttactatatt cggatatatt gctaaaattt    120
tcacaaacag aaataactgc accaataatg ccattggatt gtgcaaacgc atcaaatgtt    180
caggctgtga accgttctgc agcaaaaggg gtgacacttc ttctcccaga accggagtgg    240
acataccctc gtttatcttg cccgggctca acctttcaga aagcactcct aattagcccc    300
catagattcg gagaaaccaa ggaaactca gctcccttga taataaggga acctttttatt    360 gcttgtggac caacggaatg caaacacttt gctctaaccc attatgcagc tcaaccaggg    420
ggatactaca atggaacaag agaagacaga aacaagctga ggcatctaat ttcagtcaaa    480
ttgggcaaaa tcccaacagt agaaaactcc attttccata tggcagcttg agcgggtcc    540 gcatgccatg atggtaaaga atggacatat atcggagttg atggcccga cagtaatgca    600 ttactcaaaa taaaatatgg agaagcatat actgacacat accattccta tgcaaaaaac    660
atcctaagga cacaagaaag tgcctgcaat tgcatcgggg gagattgtta tcttatgata    720
actgatggcc cagcttcagg gattagtgaa tgcagattcc ttaagattcg agagggccga    780
ataataaaag aaatatttcc aacaggaaga gtaaaacata ctgaggaatg cacatgcgga    840
tttgccagca caaaaccat agaatgtgct tgtagagata cagttacac agcaaaaaga    900 cccttttgtca aattaaatgt ggagactgat acagcggaaa taagattgat gtgcacagag    960
acttatttgg acacccccag accaaatgat ggaagcataa cagggccttg cgaatctgat   1020
ggggacaaag ggagtggagg catcaaggga ggatttgttc atcaaagaat ggcatccaag   1080
attggaaggt ggtactctcg aacgatgtct aaaactaaaa gaatggggat gggactgtat   1140
gtaaagtatg atggagaccc atggactgac agtgaagccc ttgctcttag tggagtaatg   1200
gtttcgatgg aagaacctgg ttggtattcc tttggcttcg aaataaaaga taagaaatgt   1260
gatgtcccct gtattgggat agaaatggta catgatggtg gaaaacgac ttggcactca   1320 gcagcaacag ccatttactg tttaatgggc tcaggacaac tgctgtggga cactgtcaca   1380
ggtgttgata tggctctgta a                                            1401

<210> SEQ ID NO 7
<211> LENGTH: 1447
<212> TYPE: PRT
<213> ORGANISM: Influenza B virus

<400> SEQUENCE: 7
```

-continued

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
            85                  90                  95

Thr Lys Glu Ala Leu Asp Lys Ile Glu Glu Glu Gln Asn Lys Ser Lys
        100                 105                 110

Lys Lys Ala Gln Gln Ala Ala Ala Asp Thr Gly His Ser Ser Gln Val
    115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
            165                 170                 175

Glu Gly Ala Thr Pro Gln Asp Leu Asn Thr Met Leu Asn Thr Val Gly
        180                 185                 190

Gly His Gln Ala Ala Met Gln Met Leu Lys Glu Thr Ile Asn Glu Glu
    195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
        260                 265                 270

Ile Val Arg Met Tyr Ser Pro Thr Ser Ile Leu Asp Ile Arg Gln Gly
    275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
        340                 345                 350

Val Gly Gly Pro Gly His Lys Ala Arg Val Leu Ala Glu Ala Met Ser
    355                 360                 365

Gln Val Thr Asn Ser Ala Thr Ile Met Met Gln Arg Gly Asn Phe Arg
    370                 375                 380

Asn Gln Arg Lys Ile Val Lys Cys Phe Asn Cys Gly Lys Glu Gly His
385                 390                 395                 400

Ile Ala Arg Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
        420                 425                 430
```

```
                    -continued

Phe Leu Arg Glu Asp Leu Ala Phe Leu Gln Gly Lys Ala Arg Glu Phe
                435                 440                 445

Ser Ser Glu Gln Thr Arg Ala Asn Ser Pro Thr Ile Ser Ser Glu Gln
        450                 455                 460

Thr Arg Ala Asn Ser Pro Thr Arg Arg Glu Leu Gln Val Trp Gly Arg
        465                 470                 475                 480

Asp Asn Asn Ser Leu Ser Glu Ala Gly Ala Asp Arg Gln Gly Thr Val
                        485                 490                 495

Ser Phe Asn Phe Pro Gln Ile Thr Leu Trp Gln Arg Pro Leu Val Thr
            500                 505                 510

Ile Lys Ile Gly Gly Gln Leu Lys Glu Ala Leu Leu Asp Thr Gly Ala
        515                 520                 525

Asp Asp Thr Val Leu Glu Glu Met Ser Leu Pro Gly Arg Trp Lys Pro
        530                 535                 540

Lys Met Ile Gly Gly Ile Gly Gly Phe Ile Lys Val Arg Gln Tyr Asp
        545                 550                 555                 560

Gln Ile Leu Ile Glu Ile Cys Gly His Lys Ala Ile Gly Thr Val Leu
                        565                 570                 575

Val Gly Pro Thr Pro Val Asn Ile Ile Gly Arg Asn Leu Leu Thr Gln
                    580                 585                 590

Ile Gly Cys Thr Leu Asn Phe Pro Ile Ser Pro Ile Glu Thr Val Pro
                595                 600                 605

Val Lys Leu Lys Pro Gly Met Asp Gly Pro Lys Val Lys Gln Trp Pro
        610                 615                 620

Leu Thr Glu Glu Lys Ile Lys Ala Leu Val Glu Ile Cys Thr Glu Met
        625                 630                 635                 640

Glu Lys Glu Gly Lys Ile Ser Lys Ile Gly Pro Glu Asn Pro Tyr Asn
                        645                 650                 655

Thr Pro Val Phe Ala Ile Lys Lys Lys Asp Ser Thr Lys Trp Arg Lys
                    660                 665                 670

Leu Val Asp Phe Arg Glu Leu Asn Lys Arg Thr Gln Asp Phe Trp Glu
                675                 680                 685

Val Gln Leu Gly Ile Pro His Pro Ala Gly Leu Lys Lys Lys Lys Ser
            690                 695                 700

Val Thr Val Leu Asp Val Gly Asp Ala Tyr Phe Ser Val Pro Leu Asp
        705                 710                 715                 720

Glu Asp Phe Arg Lys Tyr Thr Ala Phe Thr Ile Pro Ser Ile Asn Asn
                        725                 730                 735

Glu Thr Pro Gly Ile Arg Tyr Gln Tyr Asn Val Leu Pro Gln Gly Trp
                    740                 745                 750

Lys Gly Ser Pro Ala Ile Phe Gln Ser Ser Met Thr Lys Ile Leu Glu
                755                 760                 765

Pro Phe Arg Lys Gln Asn Pro Asp Ile Val Ile Tyr Gln Tyr Met Asp
            770                 775                 780

Asp Leu Tyr Val Gly Ser Asp Leu Glu Ile Gly Gln His Arg Thr Lys
        785                 790                 795                 800

Ile Glu Glu Leu Arg Gln His Leu Leu Arg Trp Gly Leu Thr Thr Pro
                        805                 810                 815

Asp Lys Lys His Gln Lys Glu Pro Pro Phe Leu Trp Met Gly Tyr Glu
                    820                 825                 830

Leu His Pro Asp Lys Trp Thr Val Gln Pro Ile Val Leu Pro Glu Lys
                835                 840                 845

Asp Ser Trp Thr Val Asn Asp Ile Gln Lys Leu Val Gly Lys Leu Asn
            850                 855                 860
```

-continued

```
Trp Ala Ser Gln Ile Tyr Pro Gly Ile Lys Val Arg Gln Leu Cys Lys
865                 870                 875                 880

Leu Leu Arg Gly Thr Lys Ala Leu Thr Glu Val Ile Pro Leu Thr Glu
                885                 890                 895

Glu Ala Glu Leu Glu Leu Ala Glu Asn Arg Glu Ile Leu Lys Glu Pro
            900                 905                 910

Val His Gly Val Tyr Tyr Asp Pro Ser Lys Asp Leu Ile Ala Glu Ile
            915                 920                 925

Gln Lys Gln Gly Gln Gly Gln Trp Thr Tyr Gln Ile Tyr Gln Glu Pro
        930                 935                 940

Phe Lys Asn Leu Lys Thr Gly Lys Tyr Ala Arg Thr Arg Gly Ala His
945                 950                 955                 960

Thr Asn Asp Val Lys Gln Leu Thr Glu Ala Val Gln Lys Ile Thr Thr
                965                 970                 975

Glu Ser Ile Val Ile Trp Gly Lys Thr Pro Lys Phe Lys Leu Pro Ile
            980                 985                 990

Gln Lys Glu Thr Trp Glu Thr Trp Trp Thr Glu Tyr Trp Gln Ala Thr
        995                 1000                1005

Trp Ile Pro Glu Trp Glu Phe Val Asn Thr Pro Pro Leu Val Lys
    1010                1015                1020

Leu Trp Tyr Gln Leu Glu Lys Glu Pro Ile Val Gly Ala Glu Thr
    1025                1030                1035

Phe Tyr Val Asp Gly Ala Ala Ser Arg Glu Thr Lys Leu Gly Lys
    1040                1045                1050

Ala Gly Tyr Val Thr Asn Arg Gly Arg Gln Lys Val Val Thr Leu
    1055                1060                1065

Thr Asp Thr Thr Asn Gln Lys Thr Glu Leu Gln Ala Ile His Leu
    1070                1075                1080

Ala Leu Gln Asp Ser Gly Leu Glu Val Asn Ile Val Thr Asp Ser
    1085                1090                1095

Gln Tyr Ala Leu Gly Ile Ile Gln Ala Gln Pro Asp Lys Ser Glu
    1100                1105                1110

Ser Glu Leu Val Asn Gln Ile Ile Glu Gln Leu Ile Lys Lys Glu
    1115                1120                1125

Lys Val Tyr Leu Ala Trp Val Pro Ala His Lys Gly Ile Gly Gly
    1130                1135                1140

Asn Glu Gln Val Asp Lys Leu Val Ser Ala Gly Ile Arg Lys Val
    1145                1150                1155

Leu Phe Leu Asp Gly Ile Asp Lys Ala Gln Asp Glu His Glu Lys
    1160                1165                1170

Tyr His Ser Asn Trp Arg Ala Met Ala Ser Asp Phe Asn Leu Pro
    1175                1180                1185

Pro Val Val Ala Lys Glu Ile Val Ala Ser Cys Asp Lys Cys Gln
    1190                1195                1200

Leu Lys Gly Glu Ala Met His Gly Gln Val Asp Cys Ser Pro Gly
    1205                1210                1215

Ile Trp Gln Leu Asp Cys Thr His Leu Glu Gly Lys Val Ile Leu
    1220                1225                1230

Val Ala Val His Val Ala Ser Gly Tyr Ile Glu Ala Glu Val Ile
    1235                1240                1245

Pro Ala Glu Thr Gly Gln Glu Thr Ala Tyr Phe Leu Leu Lys Leu
    1250                1255                1260

Ala Gly Arg Trp Pro Val Lys Thr Ile His Thr Asp Asn Gly Ser
    1265                1270                1275
```

```
Asn Phe Thr Ser Thr Thr Val Lys Ala Ala Cys Trp Trp Ala Gly
    1280                1285                1290

Ile Lys Gln Glu Phe Gly Ile Pro Tyr Asn Pro Gln Ser Gln Gly
    1295                1300                1305

Val Val Glu Ser Met Asn Lys Glu Leu Lys Lys Ile Ile Gly Gln
    1310                1315                1320

Val Arg Asp Gln Ala Glu His Leu Lys Thr Ala Val Gln Met Ala
    1325                1330                1335

Val Phe Ile His Asn Phe Lys Arg Lys Gly Gly Ile Gly Gly Tyr
    1340                1345                1350

Ser Ala Gly Glu Arg Ile Val Asp Ile Ile Ala Thr Asp Ile Gln
    1355                1360                1365

Thr Lys Glu Leu Gln Lys Gln Ile Thr Lys Ile Gln Asn Phe Arg
    1370                1375                1380

Val Tyr Tyr Arg Asp Ser Arg Asp Pro Leu Trp Lys Gly Pro Ala
    1385                1390                1395

Lys Leu Leu Trp Lys Gly Glu Gly Ala Val Val Ile Gln Asp Asn
    1400                1405                1410

Ser Asp Ile Lys Val Val Pro Arg Arg Lys Ala Lys Ile Ile Arg
    1415                1420                1425

Asp Tyr Gly Lys Gln Met Ala Gly Asp Asp Cys Val Ala Ser Arg
    1430                1435                1440

Gln Asp Glu Asp
    1445

<210> SEQ ID NO 8
<211> LENGTH: 584
<212> TYPE: PRT
<213> ORGANISM: Influenza B Virus

<400> SEQUENCE: 8

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Asn Leu Lys Gly Thr Arg Thr
        50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190
```

Tyr Ile Cys Thr Glu Gly Glu Asp Gln Ile Thr Val Trp Gly Phe His
         195                 200                 205

Ser Asp Asn Lys Thr Gln Met Lys Asn Leu Tyr Gly Asp Ser Asn Pro
210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
             245                 250                 255

Ser Gly Arg Ile Val Asp Tyr Met Met Gln Lys Pro Gly Lys Thr
         260                 265                 270

Gly Thr Ile Val Tyr Gln Arg Gly Val Leu Leu Pro Gln Lys Val Trp
         275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
             325                 330                 335

Ile Trp Val Lys Thr Pro Leu Lys Leu Ala Asn Gly Thr Lys Tyr Arg
         340                 345                 350

Pro Pro Ala Lys Leu Leu Lys Glu Arg Gly Phe Phe Gly Ala Ile Ala
         355                 360                 365

Gly Phe Leu Glu Gly Gly Trp Glu Gly Met Ile Ala Gly Trp His Gly
370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
             405                 410                 415

Ser Glu Leu Glu Val Lys Asn Leu Gln Arg Leu Ser Gly Ala Met Asp
         420                 425                 430

Glu Leu His Asn Glu Ile Leu Glu Leu Asp Glu Lys Val Asp Asp Leu
         435                 440                 445

Arg Ala Asp Thr Ile Ser Ser Gln Ile Glu Leu Ala Val Leu Leu Ser
450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
             485                 490                 495

Gly Cys Phe Glu Thr Lys His Lys Cys Asn Gln Thr Cys Leu Asp Arg
         500                 505                 510

Ile Ala Ala Gly Thr Phe Asn Ala Gly Glu Phe Ser Leu Pro Thr Phe
         515                 520                 525

Asp Ser Leu Asn Ile Thr Ala Ala Ser Leu Asn Asp Asp Gly Leu Asp
530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
             565                 570                 575

Asn Val Ser Cys Ser Ile Cys Leu
             580

<210> SEQ ID NO 9
<211> LENGTH: 466
<212> TYPE: PRT
<213> ORGANISM: Influenza B Virus

<400> SEQUENCE: 9

```
Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Gln Thr Glu Ile Thr Ala Pro
        35                  40                  45

Ile Met Pro Leu Asp Cys Ala Asn Ala Ser Asn Val Gln Ala Val Asn
    50                  55                  60

Arg Ser Ala Ala Lys Gly Val Thr Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Ile Ala Cys Gly Pro Thr Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Lys Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asn Asp Gly Ser Ile Thr Gly Pro
                325                 330                 335

Cys Glu Ser Asp Gly Asp Lys Gly Ser Gly Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415
```

```
Asp Lys Lys Cys Asp Val Pro Cys Ile Gly Ile Glu Met Val His Asp
            420                 425                 430
Gly Gly Lys Thr Thr Trp His Ser Ala Ala Thr Ala Ile Tyr Cys Leu
        435                 440                 445
Met Gly Ser Gly Gln Leu Leu Trp Asp Thr Val Thr Gly Val Asp Met
    450                 455                 460
Ala Leu
465

<210> SEQ ID NO 10
<211> LENGTH: 1233
<212> TYPE: PRT
<213> ORGANISM: Artificial Sequence
<220> FEATURE:
<223> OTHER INFORMATION: SARS/S chimeric HA TM/CY

<400> SEQUENCE: 10

Met Phe Ile Phe Leu Leu Phe Leu Thr Leu Thr Ser Gly Ser Asp Leu
1               5                   10                  15
Asp Arg Cys Thr Thr Phe Asp Asp Val Gln Ala Pro Asn Tyr Thr Gln
            20                  25                  30
His Thr Ser Ser Met Arg Gly Val Tyr Tyr Pro Asp Glu Ile Phe Arg
        35                  40                  45
Ser Asp Thr Leu Tyr Leu Thr Gln Asp Leu Phe Leu Pro Phe Tyr Ser
    50                  55                  60
Asn Val Thr Gly Phe His Thr Ile Asn His Thr Phe Gly Asn Pro Val
65                  70                  75                  80
Ile Pro Phe Lys Asp Gly Ile Tyr Phe Ala Ala Thr Glu Lys Ser Asn
                85                  90                  95
Val Val Arg Gly Trp Val Phe Gly Ser Thr Met Asn Asn Lys Ser Gln
            100                 105                 110
Ser Val Ile Ile Ile Asn Asn Ser Thr Asn Val Val Ile Arg Ala Cys
        115                 120                 125
Asn Phe Glu Leu Cys Asp Asn Pro Phe Phe Ala Val Ser Lys Pro Met
    130                 135                 140
Gly Thr Gln Thr His Thr Met Ile Phe Asp Asn Ala Phe Asn Cys Thr
145                 150                 155                 160
Phe Glu Tyr Ile Ser Asp Ala Phe Ser Leu Asp Val Ser Glu Lys Ser
                165                 170                 175
Gly Asn Phe Lys His Leu Arg Glu Phe Val Phe Lys Asn Lys Asp Gly
            180                 185                 190
Phe Leu Tyr Val Tyr Lys Gly Tyr Gln Pro Ile Asp Val Val Arg Asp
        195                 200                 205
Leu Pro Ser Gly Phe Asn Thr Leu Lys Pro Ile Phe Lys Leu Pro Leu
    210                 215                 220
Gly Ile Asn Ile Thr Asn Phe Arg Ala Ile Leu Thr Ala Phe Ser Pro
225                 230                 235                 240
Ala Gln Asp Ile Trp Gly Thr Ser Ala Ala Ala Tyr Phe Val Gly Tyr
                245                 250                 255
Leu Lys Pro Thr Thr Phe Met Leu Lys Tyr Asp Glu Asn Gly Thr Ile
            260                 265                 270
Thr Asp Ala Val Asp Cys Ser Gln Asn Pro Leu Ala Glu Leu Lys Cys
        275                 280                 285
Ser Val Lys Ser Phe Glu Ile Asp Lys Gly Ile Tyr Gln Thr Ser Asn
    290                 295                 300
```

```
Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
            325                 330                 335

Val Tyr Ala Trp Glu Arg Lys Lys Ile Ser Asn Cys Val Ala Asp Tyr
        340                 345                 350

Ser Val Leu Tyr Asn Ser Thr Phe Phe Ser Thr Phe Lys Cys Tyr Gly
    355                 360                 365

Val Ser Ala Thr Lys Leu Asn Asp Leu Cys Phe Ser Asn Val Tyr Ala
370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735
```

```
Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
            770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                    805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                    885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
            930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
            965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile Arg Ala Ser Ala Asn Leu Ala Ala
            995                 1000                1005

Thr Lys Met Ser Glu Cys Val Leu Gly Gln Ser Lys Arg Val Asp
        1010                1015                1020

Phe Cys Gly Lys Gly Tyr His Leu Met Ser Phe Pro Gln Ala Ala
        1025                1030                1035

Pro His Gly Val Val Phe Leu His Val Thr Tyr Val Pro Ser Gln
        1040                1045                1050

Glu Arg Asn Phe Thr Thr Ala Pro Ala Ile Cys His Glu Gly Lys
        1055                1060                1065

Ala Tyr Phe Pro Arg Glu Gly Val Phe Val Phe Asn Gly Thr Ser
        1070                1075                1080

Trp Phe Ile Thr Gln Arg Asn Phe Phe Ser Pro Gln Ile Ile Thr
        1085                1090                1095

Thr Asp Asn Thr Phe Val Ser Gly Asn Cys Asp Val Val Ile Gly
        1100                1105                1110

Ile Ile Asn Asn Thr Val Tyr Asp Pro Leu Gln Pro Glu Leu Asp
        1115                1120                1125

Ser Phe Lys Glu Glu Leu Asp Lys Tyr Phe Lys Asn His Thr Ser
        1130                1135                1140

Pro Asp Val Asp Leu Gly Asp Ile Ser Gly Ile Asn Ala Ser Val
        1145                1150                1155
```

Val Asn Ile Gln Lys Glu Ile Asp Arg Leu Asn Glu Val Ala Lys
    1160                1165                1170

Asn Leu Asn Glu Ser Leu Ile Asp Leu Gln Glu Leu Gly Lys Tyr
1175 1180 1185

Glu Gln Tyr Ile Lys Trp Pro Gln Ile Leu Ser Ile Tyr Ser Thr
1190 1195 1200

Val Ala Ser Ser Leu Ala Leu Ala Ile Met Met Ala Gly Leu Ser
1205 1210 1215

Leu Trp Met Cys Ser Asn Gly Ser Leu Gln Cys Arg Ile Cys Ile
1220 1225 1230

<210> SEQ ID NO 11
<211> LENGTH: 1218
<212> TYPE: DNA
<213> ORGANISM: Artificial Sequence
<220> FEATURE:
<223> OTHER INFORMATION: RSV F1 Indo TMCT

<400> SEQUENCE: 11
atggagggcg aggtgaacaa gatcaagtcc gctctgctgt ccaccaacaa ggctgtggtg 60
tccctgtcca acggtgtctc cgtgctgacc tccaaggtgc tggacctgaa gaactacatc 120
gacaagcagc tgctgcccat cgtgaacaag cagtcctgct ccatctccaa catcgagacc 180
gtgatcgagt tccagcagaa gaacaaccgt ctgctcgaga tcacccgtga gttctccgtg 240
aacgctggtg tcaccacccc cgtgtccacc tacatgctga ccaactccga gctgctgtcc 300
ctgatcaacg acatgcccat caccaacgac caaaagaagc tgatgtccaa caacgtgcag 360
atcgtgcgtc agcagtccta ctctatcatg tccatcatca aggaagaagt cctggcttac 420
gtcgtgcagc tgcccctgta cggtgtcatc gacacccccct gctggaagct gcacacctcc 480
cccctgtgca ccaccaacac caaggaaggt tccaacatct gcctgacccg taccgaccgt 540
ggttggtact gcgacaacgc tggttccgtg tccttcttcc cccaagctga gacctgcaag 600
gtgcagtcca accgtgtgtt ctgcgacacc atgaactccc tgaccctgcc ctccgagatc 660
aacctgtgca acgtggacat cttcaacccc aagtacgact gcaagatcat gacctctaag 720
accgacgtgt cctcctccgt gatcacctcc ctgggtgcta tcgtgtcctg ctacggcaag 780
accaagtgca ccgcttccaa caagaaccgc ggcatcatca agaccttctc caacggttgc 840
gactacgtgt ccaacaaggg catggacacc gtgtccgtcg gtaacaccct gtactacgtc 900
aacaagcagg aaggcaagtc tctgtacgtg aagggcgagc ccatcatcaa cttctacgac 960
cccctggtgt tcccctccga cgagttcgac gcttccatca gccaggtcaa cgagaagatc 1020
aaccagtccc tggctttcat ccgtaagtcc gacgagctgc tgcacaacgt caacgctggc 1080
aagtctacca ccaacatcat gcagatcctg tccatctact ccaccgtggc ttcctccctg 1140
gctctggcta tcatgatggc tggtctgtcc ctgtggatgt gctccaacgg ctccctgcag 1200
tgccgtatct gcatctaa 1218

<210> SEQ ID NO 12
<211> LENGTH: 405
<212> TYPE: PRT
<213> ORGANISM: Artificial Sequence
<220> FEATURE:
<223> OTHER INFORMATION: RSV F1 Indo TMCT

<400> SEQUENCE: 12

Met Glu Gly Glu Val Asn Lys Ile Lys Ser Ala Leu Leu Ser Thr Asn
1 5 10 15

```
Lys Ala Val Val Ser Leu Ser Asn Gly Val Ser Val Leu Thr Ser Lys
             20                  25                  30
Val Leu Asp Leu Lys Asn Tyr Ile Asp Lys Gln Leu Leu Pro Ile Val
         35                  40                  45
Asn Lys Gln Ser Cys Ser Ile Ser Asn Ile Glu Thr Val Ile Glu Phe
 50                  55                  60
Gln Gln Lys Asn Asn Arg Leu Leu Glu Ile Thr Arg Glu Phe Ser Val
 65                  70                  75                  80
Asn Ala Gly Val Thr Thr Pro Val Ser Thr Tyr Met Leu Thr Asn Ser
                 85                  90                  95
Glu Leu Leu Ser Leu Ile Asn Asp Met Pro Ile Thr Asn Asp Gln Lys
            100                 105                 110
Lys Leu Met Ser Asn Asn Val Gln Ile Val Arg Gln Gln Ser Tyr Ser
            115                 120                 125
Ile Met Ser Ile Ile Lys Glu Val Leu Ala Tyr Val Val Gln Leu
        130                 135                 140
Pro Leu Tyr Gly Val Ile Asp Thr Pro Cys Trp Lys Leu His Thr Ser
145                 150                 155                 160
Pro Leu Cys Thr Thr Asn Thr Lys Glu Gly Ser Asn Ile Cys Leu Thr
                165                 170                 175
Arg Thr Asp Arg Gly Trp Tyr Cys Asp Asn Ala Gly Ser Val Ser Phe
            180                 185                 190
Phe Pro Gln Ala Glu Thr Cys Lys Val Gln Ser Asn Arg Val Phe Cys
            195                 200                 205
Asp Thr Met Asn Ser Leu Thr Leu Pro Ser Glu Ile Asn Leu Cys Asn
210                 215                 220
Val Asp Ile Phe Asn Pro Lys Tyr Asp Cys Lys Ile Met Thr Ser Lys
225                 230                 235                 240
Thr Asp Val Ser Ser Ser Val Ile Thr Ser Leu Gly Ala Ile Val Ser
                245                 250                 255
Cys Tyr Gly Lys Thr Lys Cys Thr Ala Ser Asn Lys Asn Arg Gly Ile
            260                 265                 270
Ile Lys Thr Phe Ser Asn Gly Cys Asp Tyr Val Ser Asn Lys Gly Met
            275                 280                 285
Asp Thr Val Ser Val Gly Asn Thr Leu Tyr Tyr Val Asn Lys Gln Glu
        290                 295                 300
Gly Lys Ser Leu Tyr Val Lys Gly Glu Pro Ile Ile Asn Phe Tyr Asp
305                 310                 315                 320
Pro Leu Val Phe Pro Ser Asp Glu Phe Asp Ala Ser Ile Ser Gln Val
                325                 330                 335
Asn Glu Lys Ile Asn Gln Ser Leu Ala Phe Ile Arg Lys Ser Asp Glu
            340                 345                 350
Leu Leu His Asn Val Asn Ala Gly Lys Ser Thr Thr Asn Ile Met Gln
            355                 360                 365
Ile Leu Ser Ile Tyr Ser Thr Val Ala Ser Ser Leu Ala Leu Ala Ile
        370                 375                 380
Met Met Ala Gly Leu Ser Leu Trp Met Cys Ser Asn Gly Ser Leu Gln
385                 390                 395                 400
Cys Arg Ile Cys Ile
            405
```